US006238867B1

(12) United States Patent
Roninson et al.

(10) Patent No.: US 6,238,867 B1
(45) Date of Patent: May 29, 2001

(54) COMPOSITIONS, METHODS AND KITS FOR IDENTIFYING NATURALLY OCCURRING RNA SEQUENCES HAVING AFFINITY FOR RNA-BINDING PROTEINS

(75) Inventors: Igor B. Roninson, Wilmette, IL (US); Abraham Grossman, Pleasantville, NY (US)

(73) Assignee: InVitro Diagnostics Inc

( * ) Notice: Subject to any disclaimer, the term of this patent is extended or adjusted under 35 U.S.C. 154(b) by 0 days.

(21) Appl. No.: 09/255,464

(22) Filed: Feb. 22, 1999

Related U.S. Application Data

(60) Provisional application No. 60/075,495, filed on Feb. 23, 1998.

(51) Int. Cl.[7] .............................. C12Q 1/68; C12P 19/34; C07H 19/00

(52) U.S. Cl. .......................... 435/6; 435/91.2; 435/91.52; 435/91.51; 536/22.1

(58) Field of Search .......................... 536/22.1; 435/91.2, 435/91.52, 91.51, 6

(56) References Cited

U.S. PATENT DOCUMENTS 5,472,840 * 12/1995 Stefano .................................... 435/6

* cited by examiner

*Primary Examiner*—W. Gary Jones
*Assistant Examiner*—Joyce Tung
(74) *Attorney, Agent, or Firm*—Anthony J. Janiuk

(57) ABSTRACT

The present invention is directed to methods, compositions, kits and apparatus to identify and detect the presence or absence of target analytes. The embodiments of the present invention have utility in identification of protein and measurement of its levels in specimens and samples, as well as the design of test kits and apparatus for implementing such methods.

13 Claims, 14 Drawing Sheets

TO

COMPOSITIONS, METHODS AND KITS FOR IDENTIFYING NATURALLY OCCURRING RNA SEQUENCES HAVING AFFINITY FOR RNA-BINDING PROTEINS

This application is a continuing application based on a provisional application, Ser. No. 60/075,495, of the same title, filed Feb. 23, 1998.

FIELD OF THE INVENTION

The present invention is directed to methods, compositions, kits and apparatus to identify ribonucleic acid (RNA) molecules having a consensus sequence exhibiting affinity for RNA binding proteins. And, the present invention is directed to compositions, methods, kits and apparatus to identify proteins which exhibit affinity to consensus sequences of RNA molecules which have affinity for RNA-binding proteins. Embodiments of the present invention have utility in the identification of RNA-binding proteins and/or RNA molecules having affinity for consensus sequences of RNA-binding proteins. Embodiments of the present invention have utility in the determination of the presence, absence or concentration of such RNA molecules and or such proteins in specimens and samples.

BACKGROUND OF THE INVENTION

In living cells, RNA is normally associated with proteins to form various nucleoprotein complexes (RNPs). These RNAs are sometimes referred to as splicosomal RNA; ribosomal RNA (rRNA); RNA-associated enzymes, such as RNAses, RNA ligases and telomerase; messenger RNA (mRNA); transfer RNA (tRNA); heterogenous nuclear RNA (hnRNA); and small nuclear RNA (snRNA). The RNPs corresponding to such RNAs are commonly referred to with reference to similar or identical prefix designations, as in heterogenous nuclear protein complex or, simply, hnRNP. The protein component of the RNP is commonly referred to with reference to such prefix and the complex, as in heterogenous nuclear protein complex protein or, simply, hnRNP protein.

A significant portion of RNA-binding proteins mediate the post-transcriptional regulation of gene expression. Heterogenous nuclear RNAs (hnRNA) are the primary transcripts of protein coding genes. hnRNAs are processed in the nuclei of eukariotic cells and, at least a portion of such hnRNAs, become mRNAs. From the time hnRNAs emerge from the transcriptional complex, and throughout the time they are in the nucleus, they are associated with proteins termed as hnRNP proteins. Members of this family of proteins are required for multiple steps during mRNA metabolism, including pre-mRNA processing and mRNA localization, translation and stability. The majority of proteins associated with RNAs appear to be associated with hnRNAs and messenger RNAs (mRNAs) in hnRNP and mRNP complexes. However, there are numerous, less abundant proteins which are associated with other groups of RNAs (Dreyfuss et al., 1993).

Clearly, hnRNPs and other RNP complexes have great importance for cell function. And, the presence or absence of such RNP complexes, or abnormalities in such RNP complexes may have substantial implications in disease. By way of example, without limitation, the presence or absence or abnormalities in RNP complexes may be an indication of an inherited disease, cancer, prion disease, and age related disease.

Viral RNPs and their RNA and protein components define much of the disease processes associated with the virus pathogens (e.g.HIV, Dengue virus, etc.,). By way of example two viral enzymes, Tat and rev proteins, are essential in a life cycle of HIV and form an RNP. RNPs and their RNA and protein components, for both RNA and DNA viruses, have great value as diagnostic tools.

Bacterial and viral RNP complexes are attractive diagnostic targets. The RNP complexes of pathogens, and associated RNA molecules and protein components, may present much more numerous copies in a sample compared to genomic or ribosomal targets.

A need exists for analytical methods, compositions, kits and apparatus to identify and characterize new RNP complexes. Such analytical methods, compositions, kits and apparatus have utility in the diagnosis of various cancers, infectious and inherited diseases.

SUMMARY OF INVENTION

Embodiments of the present invention features methods, compositions, kits, and apparatus for identification and characterization of the RNA sequences having specific affinity to amino acid consensus sequences of RNA-binding proteins. And, embodiments of the present invention feature such means for the identification and characterization of proteins having amino acid consensus sequences having specific affinity to RNA.

As used herein, the term "consensus sequence" means RNA-binding motifs that recognize single stranded RNA secondary structural elements such as hairpin loops, bulge loops, internal loops or single-stranded regions. Most of RNP proteins have a modular structure with one or more RNA-binding domains (RBD) and one another domain that mediates interaction with another protein. The hallmarks of the RNP motif are consensus sequences located about 30 amino acids apart in RBD, composed of from hundred to several hundreds of amino acids. Most of amino acids that participate in RNA binding are located in beta-sheet surface and these structural elements of RBD appear to provide an exposed platform to which RNA binds. The RNA, when bound, remains exposed (as opposed to buried in a fold or a pocket) and accessible to other RNA processing factors. Many RNP proteins contain multiple RBDs, and can bind to more than one RNA molecule simultaneously (Kiledjian et al., 1994).

As used herein, the term "affinity" means exhibiting an attraction or capable of binding. A specific affinity is an attraction which is directed to a particular feature or sequence of a molecule.

One embodiment of the present invention is a composition. The composition comprises a first ribonucleic acid (RNA) molecule and a second RNA molecule. The first RNA molecule is capable of binding to a RNA-binding protein and has the following formula:

5'-A-B-C-3'.

As used above, the letter "A" represents a section of the RNA molecule having 10–100,000 nucleotides, which section can be received by an RNA replicase and with another RNA sequence, F, being replicated. The letter "B" denotes a section of the RNA molecule having approximately 10 to 3,000 and more preferred 15 to 1,000, and more preferred 30 to 100 nucleotides in a first sequence having an affinity to at least one amino acid consensus sequence of RNA-binding protein, which section is capable of binding to such protein molecule. The letter "C" denotes a section of the RNA molecule having approximately 1 to 20 nucleotides which section is capable of being ligated to another RNA sequence, "D". The second RNA molecule is capable of binding to a RNA-binding protein and has the following formula:

5'-D-E-F-3'.

As used above, the letter "D" is a section of the RNA molecule having approximately 1 to 20 nucleotides, which section is capable of being ligated to another RNA sequence, "C". The letter "E" denotes a section of the RNA molecule having approximately 10 to 3000, and more preferred 15 to 1,000, and more preferred 30 to 100, nucleotides in a second sequence having an affinity to another amino acid consensus sequence of the same RNA-binding protein to which the section B exhibits affinity. Section E is capable of binding to such RNA-binding protein. The letter "F" denotes a section of the RNA molecule having 10–100,000 nucleotides which section is capable of being received by an RNA replicase and with another sequence, "A", being replicated. The first and the second RNA molecules are differ in their composition, such as they have two different parts of RNA replicase template. Neither of these parts can serve separately as an amplifiable template for RNA replicase.The first and the second RNA molecules capable of forming a third, hybrid RNA molecule having the following formula:

5'-A-B-C-D-E-F-3'.

The third RNA molecule is formed by ligating the C and D sections, as the E and the B sections are bound to the two consensus sequences of the same RNA-binding protein. The third RNA molecule is capable of being received by an RNA replicase and being replicated by such enzyme.

The sequences represented by the letters A, B, C, D, E, and F may further comprise sequences and nucleotides which are artifacts of cloning, synthesis or naturally occurring nucleotides.

Preferably, the sequences represented by the letters "A" and "F" are selected from the group of sequences consisting of any Q-beta RNA template. RNA sequences which can serve as a template comprise, by way of example, and not by limitation, microvariant RNA, nanovariant RNA, midivariant RNA and modifications of such sequences that maintain the ability of the sequences to be replicated by RNA replicase. Preferably, the replicase is Q-beta replicase.

Preferably, the sections B and E each are sections having 10–3000 nucleotides, and more preferred 15 to 1,000, and, even more preferred, 30 to 100 nucleotides having a sequence of the RNA component of naturally occurring RNA sequences that have affinity to different amino acid consensus sequences of the same RNA-binding protein. A preferred RNA-binding protein is any, without limitation, RNP protein of human and livestock, virus or viral complex, specific cellular and bacterial organelles, various protein-RNA complexes involved in the regulation of transcription, RNA processing or translation in normal cells or during malignancies and cell transformation. Preferably, the sections B and E bind to the consensus protein component through non-nucleic acid base pairing interactions. Furthermore, the B and E sections are selected for a particular functionality, such as binding to certain consensus sequence of an RNA-binding protein. And most preferably B and E sections are RNA or part RNA of known sequences or RNA sequences selected from the total or fractionated RNA libraries of natural origin. As used herein, "of natural origin" means derived from living organisms, by way of example, without limitation, derived from animal, fungal, algal, protozoan, plant, viruses or bacterial sources, including cells or organelles.

Preferably, the sequence of the section E is selected from the same RNA library as B; however, section E is different from section B. The interaction of the sections B and E with respect of their specificities to bind an RNA-binding protein is similar to nucleic acid probe-nucleic acid analyte hybridization, or antibody-antigen interaction.

Preferably, each section C and D has 1 to 20 nucleotides.

An embodiment of the present invention further comprises a method of making a first RNA molecule and a second RNA molecule wherein the first RNA molecule has the formula:

5'-A-B-C-3' and the second RNA molecule has the formula:

5'-D-E-F-3'.

As used above, the letters A, B, C, D, E, and F are as previously described.

The method comprises the steps of providing an original DNA library. Preferably, the original DNA library is provided as cDNA or genomic DNA of a specific gene, or total cellular cDNA, which may be subjected to normalization to decrease the redundancy of more abundant sequences. Preferably, the original DNA library encodes the sequences of RNA molecules that naturally interact with the RNA-binding protein(s). The original cDNA is constructed from cellular RNA pool and preferably from total, rather than a poly(A) selected RNA pool. Preferably, the original genomic DNA is fragmented by mechanical shearing or by enzymatic digestion in a sequence non-specific manner to the average size of 10 to 3,000 and preferably 15 to 1,000 and most preferably of 30 to 100 base pairs (bp).

The method further comprises the step of constructing a first recombinant plasmid DNA library and a second recombinant plasmid DNA library from the original DNA library. The original DNA library is cloned in a suitable original recombinant plasmid containing an insert of Q-beta replicase template, an RNA transcription promoter and suitable restriction sites. The original DNA library is divided in two parts to form the first and second recombinant plasmid DNA libraries and cloned in two cloning vectors derived from the original recombinant plasmid after digestion of the plasmid with the appropriate restriction enzymes.

The method further comprises the step of transcribing the first and second recombinant plasmid libraries to form a first RNA library and a second RNA library. The first RNA library comprises first RNA molecules with differing sequences comprising the B section of the molecules. The second RNA library comprises second RNA molecules with differing sequences comprising the E section. The first and second RNA libraries are generated after digestion of the first and second recombinant DNA plasmid libraries with one or more appropriate restriction enzymes and transcription of these digests using T7 RNA transcription promoter.

Preferably, in constructing the recombinant plasmid libraries, cDNA is carried as part of an insert of the Q-beta template of the original recombinant plasmid. The organization of the whole insert in the original recombinant plasmid is:

5'-L-M-Q1-N-Q2-P-3'.

The letters "M", "N" and "P" represent the restriction sites for generating the first and second vectors for cloning the original DNA library. The letter "L" represents T7 RNA promoter sequence, the site of the promoter of RNA transcription. The letter "Q1" represents a sequence which encodes a part of a Q-beta replicase template which corresponds to section A of the first RNA molecule. The letter "Q2" represents a sequence which encodes another part of a Q-beta replicase template which corresponds to the section F of the second RNA molecule.

The original recombinant plasmid having the cDNA insert encoded within a Q-beta replicase template is used to transform competent bacterial cells. The cells are cultured, harvested and the dsDNA of the original recombinant DNA plasmid isolated. The original plasmid's DNA is subjected to restriction enzyme digestion and recombination with the original DNA library to form a first recombinant DNA plasmid library and a second recombinant DNA plasmid library. The organization of the inserts in the first recombinant DNA plasmid library is set forth below:

5'-L-M-Q1-N-O-P-3'.

The organization of the inserts in the second recombinant DNA plasmid library is set forth below:

5'-L-M-R-N-Q2-P-3'

As used above, the letter "O" represents a DNA sequence encoding B and the letter "R" represents a DNA sequence encoding E. The letters "M," "N" and "P" represent restriction site linkers. The letter "P" further represents a nucleotide sequence that encodes the section C of the first RNA molecule. The letter "M" represents also a nucleotide sequence that encodes the section D of the second RNA molecule. The original DNA library is joined with sequences of a cDNA representing Q-beta template using N and P restriction sites for the first recombinant DNA plasmid library, and M and N restriction sites for the second recombinant DNA plasmid library.

The first and second recombinant DNA plasmid libraries containing the sequences of original DNA library are used to transform competent bacterial cells. The cells are cultured, harvested and dsDNAs of the first and second recombinant plasmid libraries isolated.

The organization and composition of the first recombinant RNAs of the first RNA library, transcribed from the first recombinant DNA plasmid library is described more fully below. After digestion of the first recombinant DNA plasmid library with P restriction enzyme and, using T7 RNA promoter and T7 RNA polymerase, the first recombinant RNAs of the first RNA library is formed, as set forth below:

5'-A-B-C-3'

The organization and composition of the second recombinant RNAs transcribed from the second recombinant DNA plasmid library is set forth more fully below. After digestion of the second recombinant DNA plasmid library with P restriction enzyme and, using T7 RNA promoter and T7 RNA polymerase, the second recombinant RNAs of the first RNA library is formed, as set forth below:

5'-D-E-F-3'.

The letters A, B, C. D, E, and F are as previously described. Each member of the first RNA or second RNA library contain a corresponding part of Q-beta replicase template and none of these RNA molecules of the first and second recombinant RNA libraries can be individually amplified by Q-beta replicase.

A further embodiment of the present invention features a method for selection of first and second RNA molecules binding RNA-binding protein and identification of RNA sequences capable of binding to consensus sequences of RNA-binding protein. The method comprises the steps of providing a first RNA library and a second RNA library. RNA molecules of the first library comprise first RNA molecules having the formula:

5'-A-B-C-3'.

The sections A, B and C are as previously described. RNA molecules of the second library comprise second RNA molecules having the formula:

5'-D-E-F-3'.

The sections D, E and F are as previously described. None of molecules from the first RNA and second RNA libraries can be amplified individually by Q-beta replicase enzyme. The method further comprises the step of combining of first RNA and second RNA libraries and mixing them with a protein sample potentially containing RNA binding consensus sequences. The protein is preferably selected from the group of proteins derived from intact or dissociated viral particles, preparation of organelle specific protein, nuclear or total cellular lysates of normal, transformed or malignant cells and other sources of protein. The method further comprises the step of imposing binding conditions on the sample potentially containing RNA-binding proteins in the presence of the first and second RNA libraries. In the presence of the appropriate RNA-binding protein, certain molecules from the first and the second RNA libraries will form a ternary complex with RNA-binding protein. The method further comprises the step of imposing RNA ligase reaction conditions on the sample to form a third RNA molecule in the presence of the RNA-binding protein. The third RNA molecule is amplifiable by Q-beta replicase having both parts of the templates. The third RNA molecule has the formula:

5'-A-B-C-D-E-F-3'.

Preferably, the method comprises the step of separation of the unbound RNA molecules of the first and the second RNA libraries from the third RNA molecules. After RNA ligation reaction conditions are imposed, the method comprises the further step of physical separation of the RNA molecules bound with the RNA-binding protein and non-bound RNA molecules. The reaction mixture is passed through a filter that retains the protein but not free RNA molecules. Ligated and non-ligated RNA molecules, but bound with RNA-binding protein, are co-retained with the RNA-binding protein on the filters. These RNA molecules are eluted. The signal-generating moiety is sections A and F of the third RNA molecule, which sections allow recognition and replication by RNA replicase. Preferably, the step of amplifying the bound and ligated RNA molecules is performed in the presence of the enzyme Q-beta replicase.

In the alternative, the separation step is omitted and the mixture is subjected to amplification conditions after the ligation step. The unbound and unligated first and second RNA molecules are not amplified by the enzyme Q-beta replicase. However the third RNA molecule is recognized and amplified. The amplification product can be subjected to one or more cycles of dilution and amplification to reduce the presence of the first and second RNA molecules to insignificant background.

The sample is monitored for the presence of the third RNA molecule by its amplification by Q-beta replicase. The presence of third RNA molecule is indicative of the presence of an RNA-binding protein. Preferably, at least one of the first or second RNA molecules has a signal moiety. As used herein, a signal moiety refers to a sequence, ligand, enzyme, or chemical entity capable of being detected. By way of example, without limitation, such ligand may comprise an antibody or antigen, biotin or avidin or streptavidin, or a sequence capable or binding to a probe or forming an amplification product. In the presence of the enzyme Q-beta replicase, sequences recognized by the enzyme generate an amplification product. A preferred signal moiety is a sequence recognized by the enzyme Q-beta replicase. Additional developing compositions may be applied to the reaction product, such as intercalating compounds in order to identify the amplification product. Preferably, the method further comprises the step of imposing RNA replicase conditions on the sample potentially comprising the third RNA molecule Once an amplified product made of third RNA molecules has been obtained, the cDNA corresponded to this third RNA is synthesized using reverse transcriptase enzyme. cDNA is cloned into an appropriate vector for sequencing. Sequencing of the individual clones determines the nucleotide composition of the third RNA molecule amplified by Q-beta replicase. The sequences of the first and second RNA molecules are deduced from the obtained sequences of the third RNA molecule.

A further embodiment of the present invention comprises a method for construction of the first and the second RNA molecules with known nucleotide sequences. The first and second RNA molecules will be directly transcribed from machine-synthesized first complementary DNA (cDNA) encoding the first RNA molecule and a machine synthesized second CDNA encoding the second RNA molecule.

The composition of the first CDNA representing the first recombinant RNA is:

5'-L-Q1-O-P-3'

And, the composition of the second cDNA representing the second recombinant RNA is:

5'-L-M-R-Q2-3'

Wherein the sections represented by the letters L, M, O, Q1, Q2, P, and R are as previously described.

The organization and composition of the first recombinant RNA transcribed from the first synthesized cDNA molecules using T7 RNA promoter and T7 RNA polymerase is:

5'-A-B-C-3'.

And, the organization and composition of the recombinant RNA transcribed from the second cDNA using T7 RNA promoter and T7 RNA polymerase is:

5'-D-E-F-3'.

The letters A, B, C. D, E, and F are as previously described. These two recombinant RNA transcripts are the first and the second RNA molecules.

A further embodiment of the present invention comprises a kit for determining the presence or absence of an RNA-binding protein molecule. The kit comprises one or more reagents comprising a first RNA molecule and a second RNA molecule. The first RNA molecule has the formula:

5'-A-B-C-3'.

The second RNA molecule has the formula:

5'-D-E-F-3'.

In the presence of an RNA-binding protein with affinity to the first and the second RNA molecules, the first and the second RNA molecules are capable of forming a protein-first-and-second-RNA ternary complex. In the presence of RNA ligase means and suitable ligase conditions, a third RNA molecule is formed having the formula:

5'-A-B-C-D-E-F-3'.

The letters A, B, C. D, E, and F are as previously described. The third RNA molecule is preferably capable of being received and replicated by RNA replicase. Preferably, the first and second molecules are part of RNA libraries.

Preferably, the kit further comprises other reagents, such as, RNA ligase, reverse transcriptase, suitable primers, buffers, intercalating agents and the like. As used herein the term "kit" refers to an assembly of parts, compositions and reagents with suitable packaging materials and instructions.

The present invention is further described in the following figure and examples, which illustrate features and highlight preferred embodiments and the best mode to make and use the invention.

DETAILED DESCRIPTION OF INVENTION

Figure 1:
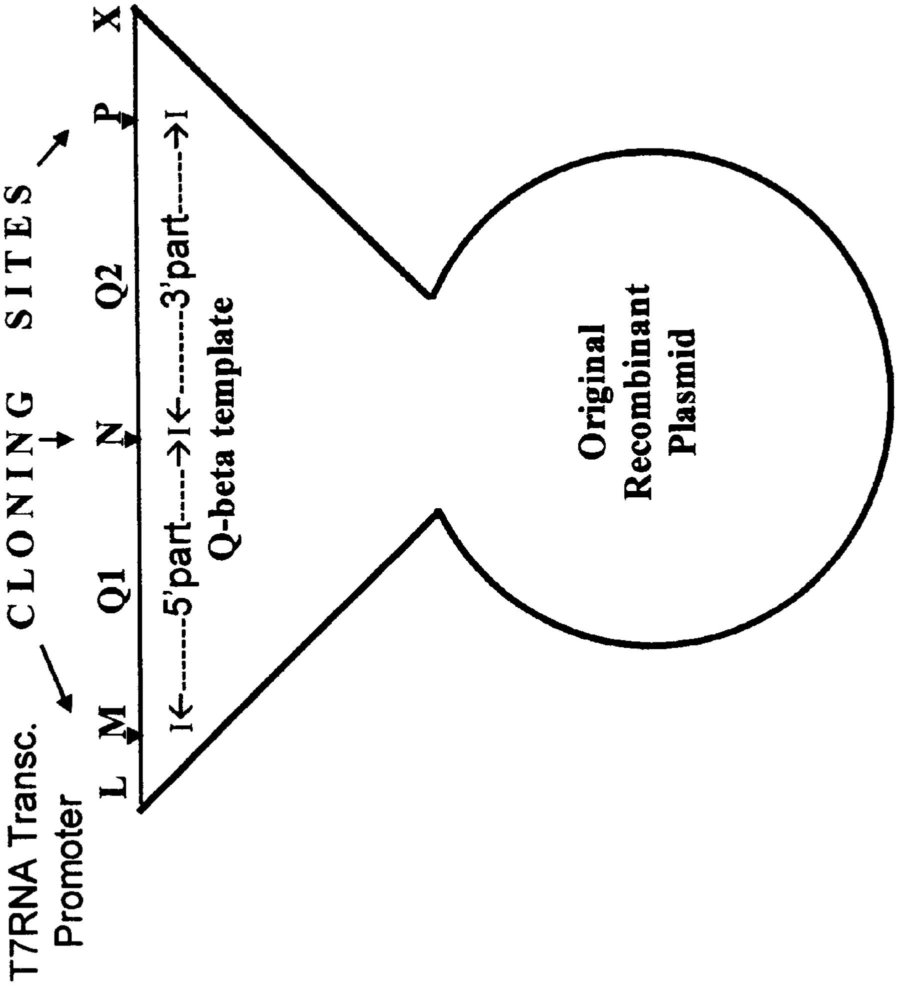
FIGS. 1*a*–1*c* depicts a flow diagram of the construction of the first and second cloning vectors.
Figure 1:
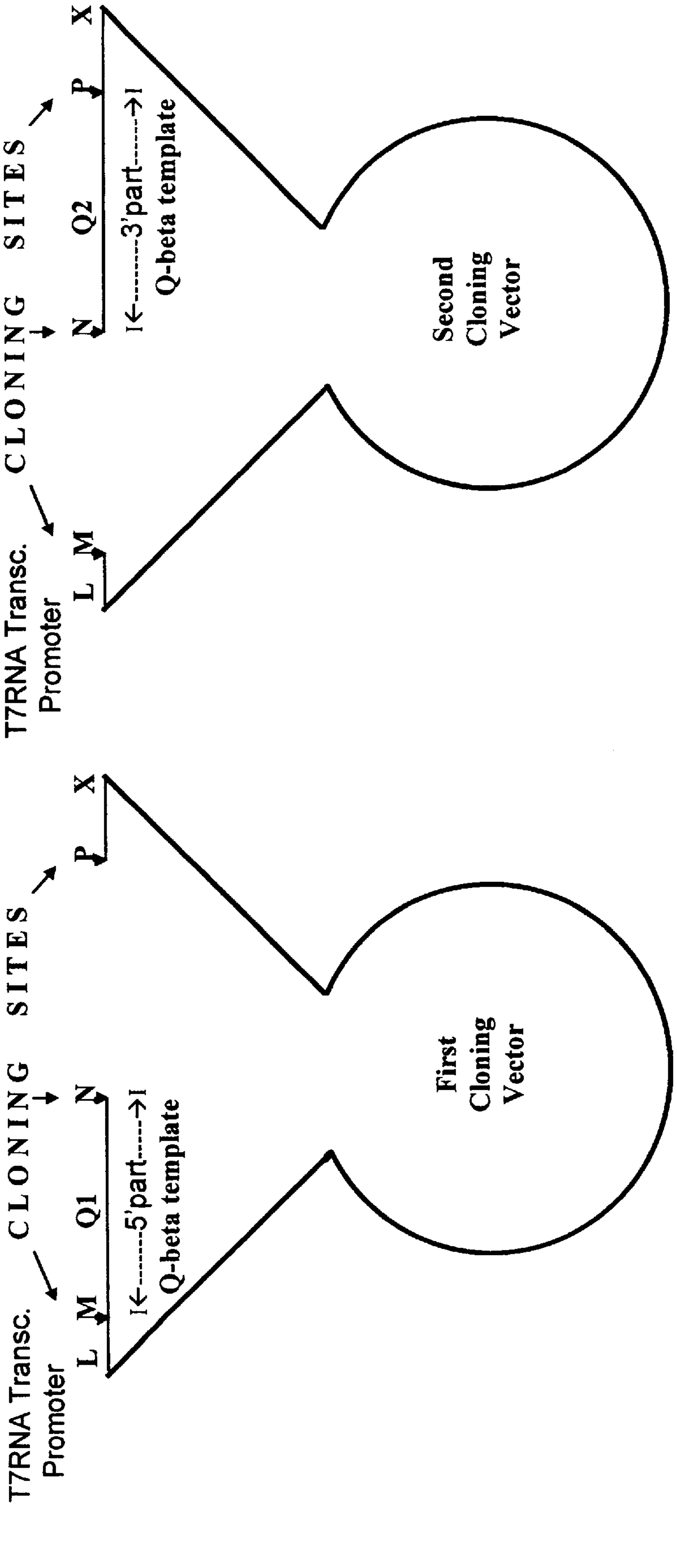
Figure 1:
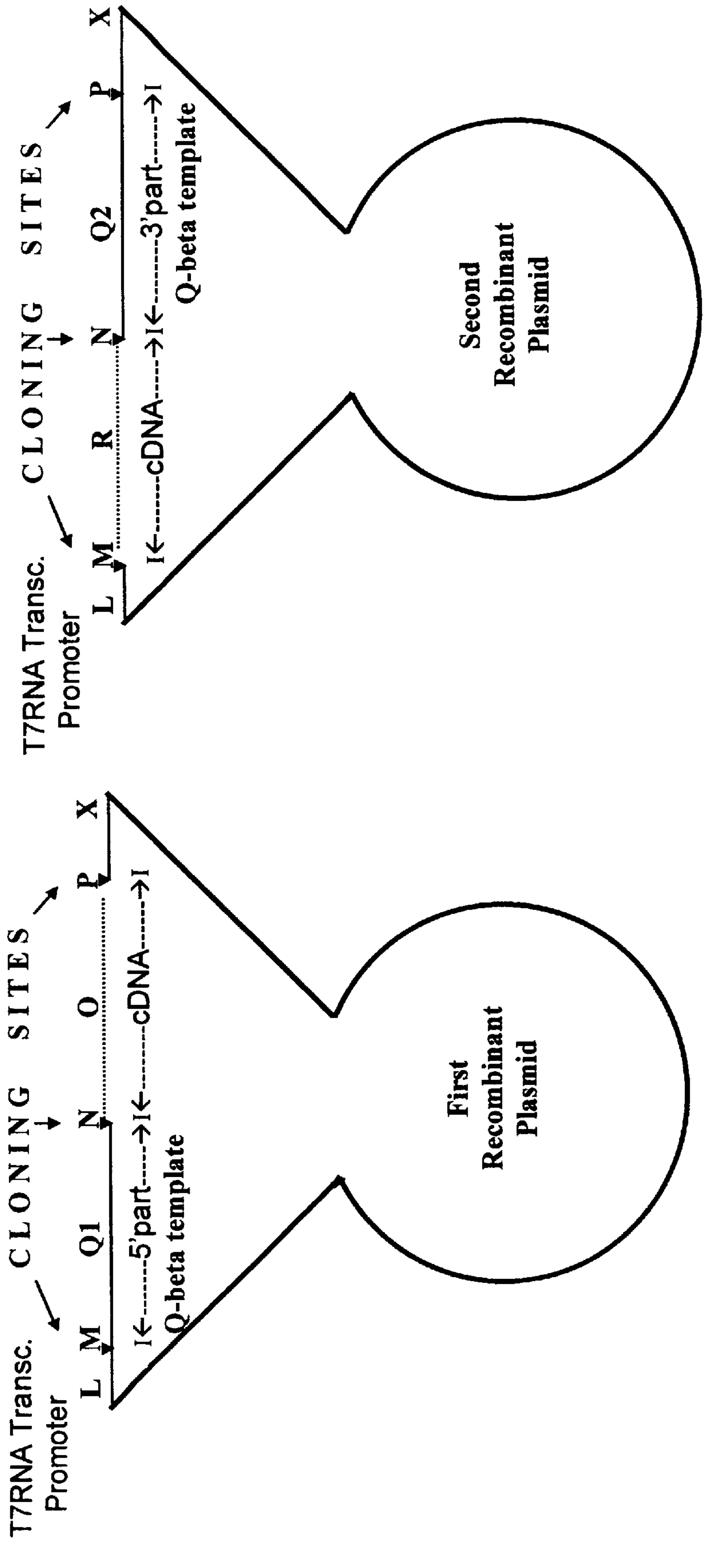
Figure 1:
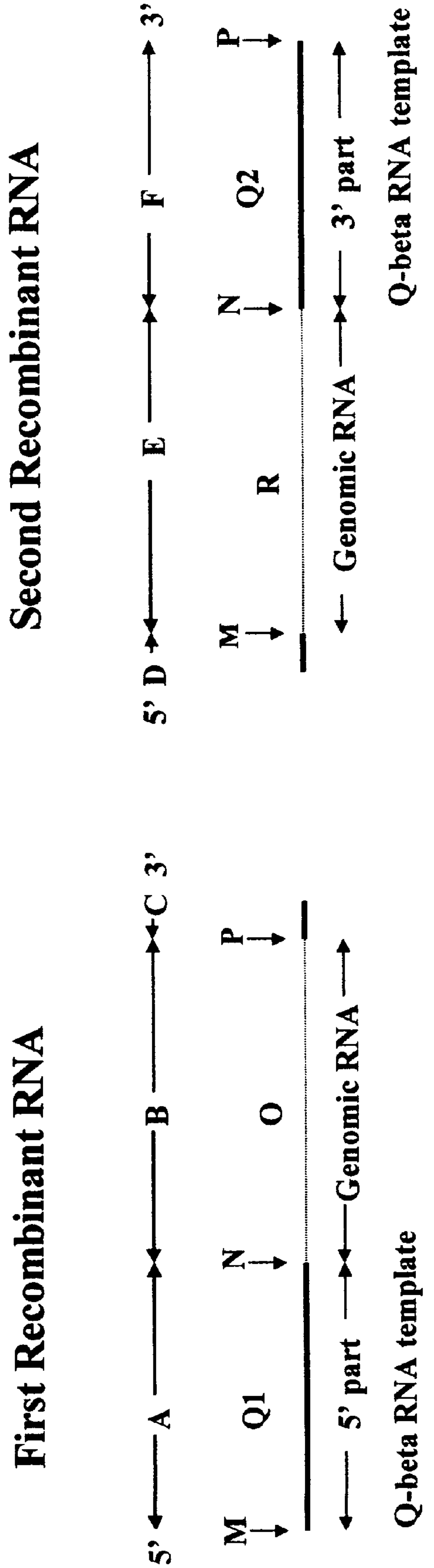
Figure 1:
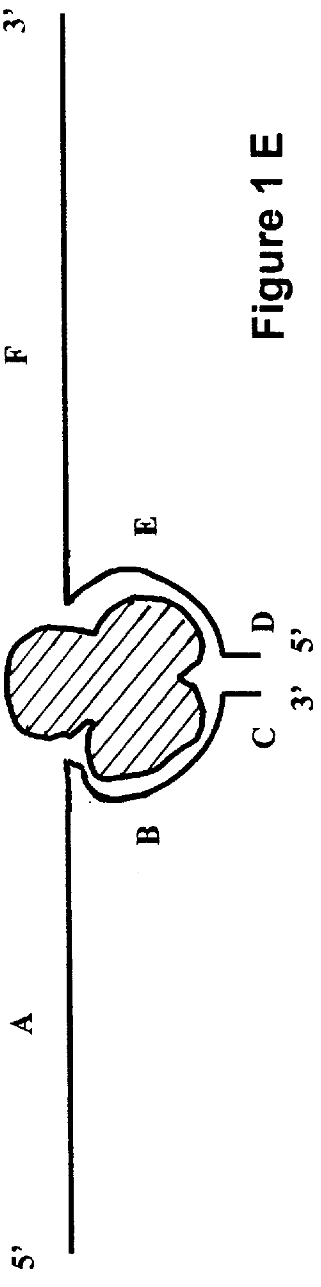
Figure 1:
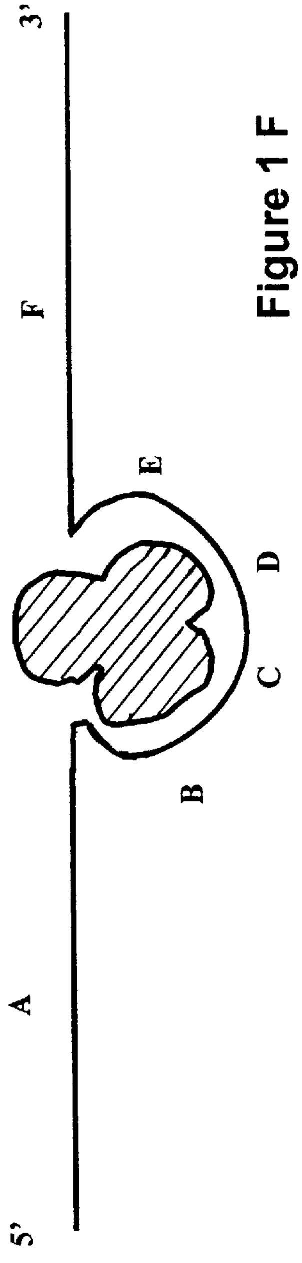
Figure 1:
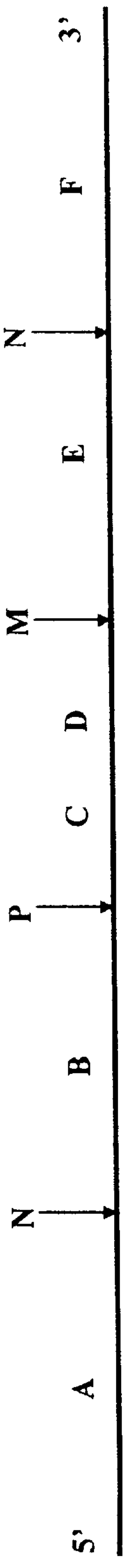

The present invention is further described in the following figures and examples, which illustrate features and highlight preferred embodiments and the best mode to make and use the invention. The present invention is directed to methods, compositions, kits and apparatus to construct nucleic acid compositions capable of forming a reaction or amplification product in the presence of RNA-binding proteins. The presence or absence of the RNA binding protein can be determined by the formation, or failure to form, a reaction or amplification product. Other features will be apparent to those skilled in the art upon reading the following description. The methods described are within the expertise of individuals skilled in the art and compositions are commercially available or can be obtained without undue experimentation.

All RNP proteins possess RNA-binding motifs. RNP proteins can bind in vitro to many different ribo- and deoxyribo-polynucleotides. Under appropriate conditions, RNP proteins can non-specifically bind to nucleic acid having gross features which are recognized by the protein without regard to particular nucleotides or nucleotide sequences. By way of example, most of heterogeneous nuclear-hnRNP proteins can be purified by affinity chromatography on ssDNA. Some of the hnRNP proteins, however, do not bind ssDNA (Matunis et al., 1994).

More stringent in vitro assays demonstrated that hnRNP proteins have different preferences for specific sequences. Binding at 2M NaCI conditions demonstrates the striking avidity of hnRNP proteins for their preferred RNAs. These results indicate that different hnRNP, and apparently other RNA-binding proteins as well can discriminate among different RNAs, and these properties provide a useful aid in isolation, purification and classification of various groups of RNA-binding proteins. Under appropriate conditions, sequence-specific RNA-binding by several hnRNP proteins has also been demonstrated by photochemical crosslinking and by RNA co-immunoprecipitation (Dreyfuss et al., 1993).

The molecular architecture of RNA-binding proteins was studied in details on hnRNP systems. The general principles of hnRNP proteins, however, are relevant to other RNA-binding proteins. Most of RNP proteins have a modular structure with one or more RNA-binding domain (RBD) and special domain(s) that mediates interaction with another protein. The hallmarks of RBD in RNA-binding protein are distinct consensus sequences separated each from another by stretches of approximately thirty amino acids. Most of amino acids that participate in RNA binding are located in beta-sheet surfaces. These particular structural elements of RBD appear to provide an exposed surface that can serve as a platform to which RNA binds. The RNA, when bound, remains exposed (as opposed to buried in binding pocket) and thus accessible to other RNA processing factors. Many RNP proteins contain multiple RBDs, and can bind to more than one RNA segment or intact RNA molecules simultaneously (Kiledjian et al., 1994).

Q-beta bacteriophage contains a plus-strand RNA. The plus-strand RNA serves as both mRNA for viral protein synthesis and a template for an RNA-dependent RNA polymerase, Q-beta replicase. In the presence of the plus-strand RNA, and other cofactors, the enzyme Q-beta replicase synthesizes the complementary minus-strand RNA. The minus-strand, in a turn, can serve as a template for plus-strand RNA synthesis. There is potential to amplify RNA molecules exponentially in the interaction between Q-beta replicase and its two templates—the plus and minus RNA molecules (Weissmann et al., 1968, Dobkin et al., 1979). Recombinant Q-beta replicase templates that form more-stable two- and three-dimensional intramolecular structures have decreased tendency to form extended plus-minus RNA-RNA duplexes during replication, which results in increased synthesis of new RNA strands (Priano et al., 1987).

Interaction of RNA and RNA-binding protein is similar to the interaction between nucleic acid probe and target molecules, as well as antibody-antigen interactions, in respect of their mutual affinity and specificity. One embodiment of the present invention is a composition. The composition comprises a first ribonucleic acid (RNA) molecule and a second RNA molecule. The first RNA molecule is capable of binding to a RNA-binding protein and has the following formula:

5'-A-B-C-3'.

The letter "A" represents a section of the RNA molecule having 10-100,000 nucleotides, which section can be received by an RNA replicase and with another RNA sequence, F, being replicated. The letter "B" denotes a section of the RNA molecule having approximately 10 to 3,000, and more preferred 15 to 1,000, and more preferred 30 to 100 nucleotides in a first sequence having an affinity to at least one amino acid consensus sequence of RNA-binding protein, which section is capable of binding to such protein molecule. The letter "C" denotes a section of the RNA molecule having approximately 1 to 20 nucleotides which section is capable of being ligated to another RNA sequence, "D". The second RNA molecule is capable of binding to RNA-binding protein and has the following formula:

5'-D-E-F-3'.

As used above, the letter "D" is a section of the RNA molecule having approximately 1 to 20 nucleotides, which section is capable of being ligated to another RNA sequence, "C". The letter "E" denotes a section of the RNA molecule having approximately 10 to 3000, and more preferred 15 to 1,000, and more preferred 30 to 100 nucleotides in a second sequence having an affinity to another amino acid consensus sequence of the same or another RBD in RNA-binding protein to which the section B exhibits affinity. The letter "F" denotes a section of the RNA molecule having 10–100,000 nucleotides which section is capable of being received by an RNA replicase and with another sequence, "A", being replicated. The first and the second RNA molecules differ in their composition; each section, A and F, has different parts of RNA replicase template. Neither of these parts can serve separately as an amplifiable template for RNA replicase. The first and the second RNA molecules capable of forming a third RNA molecule having the following formula:

5'-A-B-C-D-E-F-3'.

The RNA molecule is formed by ligating the C and D sections, as the E and the B sections are bound to the two consensus sequences of the same or different RBDs in RNA-binding protein. The third RNA molecule is capable of being received by an RNA replicase and being replicated by such enzyme.

The sequences represented by the letters A, B, C, D, E, and F may further comprise sequences and nucleotides which are artifacts of cloning or synthesis.

Preferably, the sequences selected for the sections A and F comprise a template for the enzyme Q-beta replicase. RNA sequences which can be serve as a template comprise, by way of example, without limitation, microvariant RNA, nanovariant RNA, midivariant RNA and modifications of such sequences that maintain the ability of the sequences to be replicated by Q-beta replicase. Preferably, these known sequences are divided to form the sequences of section A and F. The location of the division is a matter of convenience, influenced by existing cloning sites in the native sequence and the ability to maintain the template amplification characteristics of sequences modified to incorporate cloning sites. Neither section A or F can serve as a template for the enzyme singularly. That is, section A can not be replicated without being ligated to section F, directly or by means of other RNA sequences, and section F can not be replicated without being ligated to section A, directly or by means of other RNA sequences. A preferred sequence for section A is set forth in SEQ ID No 1 below:

SEQ ID No. 1

5'-GGGGACCCCC CCGGAAGGGG GGGACGAGGU GCGGGCACCU CGUACGGGAG UUCGACCGU GACGCUCUAG-3'

A preferred sequence for section F is set forth in SEQ ID No. 2 below:

SEQ ID No. 2

5'-AGAUCUAGAG CACGGGCUAG CGCUUUCGCG CUCUCCCAGG UGACGCCUCG UGAAGAGGCG CGACCUUCGU GCGUUUCGGU GACGCACGAG AACCGCCACG CUGCUUCGCA GCGUGGCUCC UUCGCGCAGC CCGCUGCGCG AGGUGACCCC CCGAAGGGGG GUUCCC-3'

Sequences Nos. 1 and 2 are the sequences of MDV-1 RNA template for Q-beta replicase. In the alternative, a preferred sequence for section A is set forth in SEQ ID No.3 below:

SEQ ID No. 3

5'-GGGGAAAUCC UGUUACCAGG AUAACGGGGU UUCCUCA-3'

And, a preferred sequence for section F is set forth in SQ ID No. 4 below:

SEQ ID No. 4

5'-CCUCUCUACU CGAAAGUUAG AGAGGACACA CCCGGAUCUA GCCGGGUCAA CCCA-3'

Sequences Nos. 3 and 4 are the sequences of nanovariant RNA template for Q-beta replicase.

Preferably, the sections B and E each are sections having 10–3000 nucleotides, and more preferred, 15 to 1,000, and even more preferred, 30 to 100 nucleotides having a sequence of the RNA component of naturally occurring RNA sequences that have affinity to the first or the second amino acid consensus sequences of RNA-binding protein. A preferred RNA-binding protein is any RNP protein of animal, plant, fungal, algal, viral, protozoan, bacterial or other pathogenic origin. A preferred RNA binding protein is derived from one or more viral complexes, specific cellular and bacterial organelles, various protein-RNA complexes involved in the regulation of transcription, RNA processing or translation in normal cells or during malignacies and cell transformation. Preferably, the sections B and E are selected for a particular functionality, such as binding to a certain amino acid consensus sequences of RNA-binding protein. Furthermore, the B and E sections bind to the amino acid consensus sequences of the protein component through non-nucleic acid base pairing interactions.

Preferably, B and E sections are long enough to allow to form secondary structures recognizable by the consensus sequences of the RNA-binding protein. The varied structures of RNA molecules permit diverse mechanisms for protein recognition. Preferably, RNA-binding proteins target single-stranded regions of RNA within secondary structure domains, such as hairpin loops, internal loops, symmetrical and asymmetrical bulges and pseudo-knots, where the functional groups on the nucleotides may be easily available for sequence-specific recognition by amino acid consensus sequences of RBDs.

Preferably, B and E sections are RNA or part RNA selected from the total or fractionated RNA libraries of various, without any limitation, animal or plant, fungi, algae, bacteria, viruses or microorganisms, cells or organelles. Preferably, the sequence of the section E is selected from the same RNA library as B; however, the section E is different from section B. The interaction of the sections B and E, in respect of their specificities to bind a RNA-binding protein, is similar to nucleic acid hybridization.

Preferably, each section C and D has 1 to 20 nucleotides.

An embodiment of the present invention further comprises a method of making a first RNA molecule and a second RNA molecule wherein the first RNA molecule has the formula:

5'-A-B-C-3' and the second RNA molecule has the formula:

5'-D-E-F-3'.

As used above, the letters A, B, C, D, E, and F are as previously described.

The method comprises the steps of providing an original DNA library, which DNAs containing the sequences of RNA molecules that naturally interact with protein(s). Preferably, the original DNA library is provided as cDNA or genomic DNA pools of a specific gene, or total cellular cDNA or genomic DNA pools. Preferably, the nucleic acids of the pool are subjected to normalization to decrease the redundancy of more abundant sequences and to increase representation of rare RNA molecules with affinity to RNA-binding protein of interest. Preferably, the reduction of the repeated sequences and increase of the RNA species of interest in the original DNA library is performed using gel fractionation (Partaijali et al, 1991; Gudkov et al., 1994).

In brief, DNA to be normalized is fragmented to sizes below 1,000 bp. The fragments are supplied with terminal adaptors that can be used as tags for PCR, and then denatured and allowed to reanneal for different lengths of time. At different times, aliquots are withdrawn and single-stranded and double-stranded DNA fragments are separated, e. g. by hydroxyapatite chromatography. Different single-stranded fractions are then amplified by PCR and tested for normalization by hybridization with probes corresponding to sequences that are differently represented in the initial DNA.

Preferably, the original cDNA is consructed from cellular RNA pool and, preferably, from total, rather than a poly(A), RNA pool. Poly(A) RNA represents only a fraction of the total cellular population. Preferably, the original genomic DNA and original cDNA library are fragmented by mechanical shearing or by enzymatic digestion in a sequence non-specific manner to the average size of 10 to 3,000 and, preferably, 15 to 1,000 and, most preferably, of 30 to 100 base pairs (bp). The methods of construction of cDNA libraries with random length fragments are known in the art (Gudkov et al., 1994).

The method further comprises the step of dividing the original DNA library into two parts. Turning now to FIG. 1, and, in particular, FIGS. 1*b* and *c*, one of the parts is cloned in a first cloning vector and the remaining part is cloned in a second cloning vector. Each cloning vector is prepared from an original recombinant plasmid containing a cDNA insert representing Q-beta replicase template, an RNA transcription promoter and suitable restriction sites. Preferably, the ends of DNA fragments are blunt. The ends are preferably rendered blunt by treatment with a single stranded specific nuclease. A preferred nuclease is Mung-bean nuclease or nuclease S1, which degrades single-stranded DNA at the 5' end converting the protruding termini of DNA to a blunt end. Preferably, the original recombinant plasmid is digested with PpuMI and Xho I restriction enzymes and purified from the 5' Q-beta template fragment using a gel electrophoresis method. The vector containing T7 RNA promoter and 3' Q-beta template segment will be treated with Mung-bean or S1 nucleases to generate blunt ends. This vector represents the first vector suitable for cloning the original DNA library.

In the alternative, the appropriate linkers are used to create DNA fragments suitable for cloning in the Ppu MI and Xho I sites of the first cloning vector. In this case, the Ppu MI and Xho I cloning sites of the first cloning vector remain intact. Similarly, the original recombinant plasmid is digested with Xho I and Sma I restriction enzymes and purified from the 3' Q-beta template fragment using a gel electrophoresis method. The vector containing T7 RNA promoter and 5' Q-beta template segment will be treated with Mung-bean or S1 nucleases to generate blunt ends. This vector represents the second plasmid suitable for cloning original DNA library.

As a further alternative, the appropriate linkers are used to create DNA fragments suitable for cloning in the Xho I and Sma I sites of the second cloning vector. In this case, the Xho I and Sma I cloning sites of the second cloning vector remain intact. The cloning of the original DNA library in the first and in the second cloning vectors to generate the first and second recombinant DNA plasmid libraries.

The invention further comprises the step of transcribing the first and second recombinant DNA plasmid libraries to form the first RNA and the second RNA libraries. First, the first and the second recombinant DNA plasmid libraries are digested with the appropriate restriction enzyme and then transcribed. The original recombinant plasmid is engineered to provide features to allow for these manipulations and functions.

As depicted in FIG. 1, the organization of the whole insert in the original recombinant plasmid is:

5'-L-M-Q1-N-Q2-P-3'.

The letters "M", "N" and "P" represent the restriction sites for the preparation of the first and second cloning vectors and for construction of the first and second recombinant plasmid libraries. The letter "L" represents a promoter for RNA transcription. cDNA represented Q-beta template is carried as part of an insert of the original recombinant plasmid and the letter "Q1" represents sequences which encode a part of a Q-beta replicase template which correspond to section A of the first RNA molecule. The letter "Q2" represents sequences which encode another part of a Q-beta replicase template which correspond to the section F of the second RNA molecule.

Figure 2:
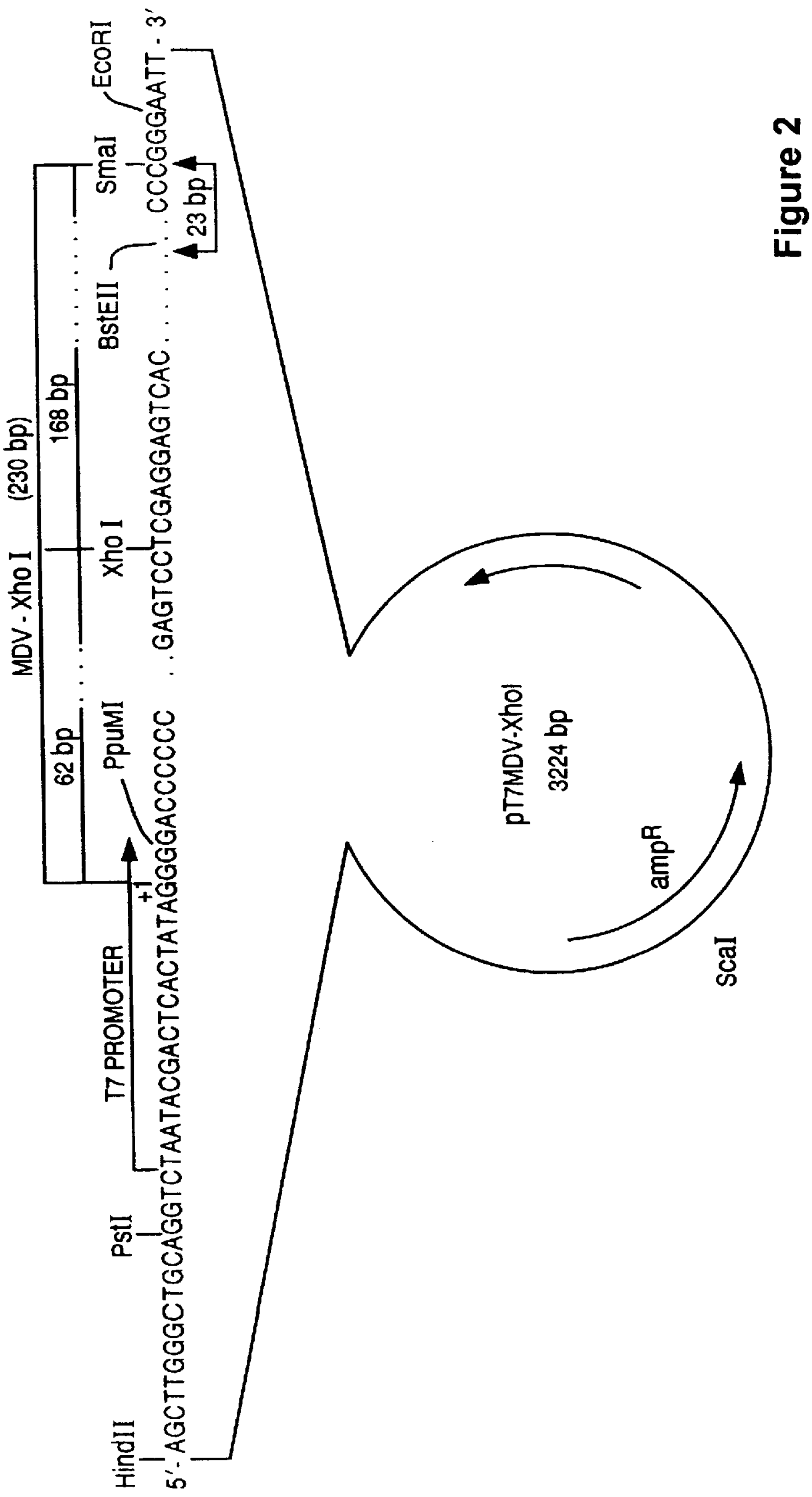
FIG. 2 depicts plasmid pT7 MDV-XhoI.

Preferably, the original plasmid used in the experiments and its construction is as described in the Examples (Axelrod et al., 1989) and shown in FIG. 2. Preferably, the letter "M", "N" and "P" represent the Ppu MI, Xho I and Sma I restriction sites, respectively. The letter "L" represents T7 RNA promoter sequence, the site of the promoter of RNA transcription. The cDNA represented MDV-I RNA template, with Q1 represented first 62 nucleotides (SEQ ID No. 1) and Q2 represented rest of 168 nucleotides of this Q-beta replicase template (SEQ ID No. 2).

The original recombinant plasmid, having the cDNA insert encoding the Q-beta replicase template, is used to transform competent bacterial cells. The cells are cultured, harvested and the dsDNA of the original recombinant plasmid isolated. The original plasmid DNAs are subjected to two sets of restriction enzyme digestions, purification from excised fragment of the Q-beta replicase template and recombination with the original DNA library to form a first recombinant plasmid and a second recombinant plasmid libraries. The organization of the inserts in the first recombinant plasmid library is set forth below:

5'-L-M-QI-N-O-P-3'.

The second recombinant plasmid library containing the 3' part of the Q-beta replicase template and sequences of the original DNA library is used to transform competent bacterial cells. The cells are cultured, harvested and dsDNAs of the second recombinant plasmid library isolated.

The organization of the inserts in the first recombinant plasmid library is set forth below:

5'-L-M-R-N-Q2-P-3'

The first recombinant plasmid library, containing the 5' part of the Q-beta replicase template and the sequences of the original DNA library, is used to transform competent bacterial cells. The cells are cultured, harvested and dsDNAs of the first recombinant plasmid library isolated. The transformation of competent bacterial cells with recombinant plasmid DNAs, the growth and harvesting of the cultured bacterial cells and isolation of recombinant plasmid DNAs is performed according to standard procedures (Sambrook et al., 1989).

The organization and composition of the first RNA molecules, which comprise the first RNA library, transcribed from the first recombinant DNA plasmid library, is set forth below. The first RNA library is formed after digestion of the first recombinant DNA plasmid library with P restriction enzyme and transcription using the T7 RNA promoter and T7 RNA polymerase.

5'-A-B-C-3'

The organization and composition of the second RNA molecules, which comprise the second RNA library, transcribed from the second recombinant DNA plasmid library, is set forth below. The second RNA library is formed after digestion of the second recombinant DNA plasmid library with P restriction enzyme and transcription using the T7 RNA promoter and T7 RNA polymerase.

5'-D-E-F-3'.

The letters A, B, C. D, E, and F are as previously described.

Preferably, digestion of the first and second recombinant DNA plasmid libraries is performed with Eco RI restriction enzyme. Each first RNA molecule comprises 5' 62 nt of the MDV-I RNA (section A), RNA sequences of the original DNA library (section B), and is terminated with GGG nucleotide triplet (section C). Each second RNA molecule comprises 168 3' nucleotides of MDV-I RNA (section F), RNA sequences representing an original DNA library (section E) and at the 5' terminus has a GGG nucleotide triplet (section D). None of the first or second type RNA molecules can be individually amplified by Q-beta replicase.

A further embodiment of the present invention features a method for selection of first and second RNA molecules from the first and second RNA libraries and identification of their nucleotide sequences capable of binding of RNA-binding protein. The method comprises the steps of providing a first RNA library comprising first RNA molecules and a second RNA library comprising second RNA molecules. First RNA molecules have the formula:

5'-A-B-C-3'.

The sections A, B and C are as previously described. Second RNA molecules have the formula:

5'-D-E-F-3'.

The sections D, E and F are as previously described. None of molecules from the first RNA and second RNA libraries can be amplified individually by Q-beta replicase enzyme.

The method further comprises the step of combining of the first RNA and second RNA libraries and mixing them with a sample containing RNA-binding protein. Preferably, the sample comprises purified protein, intact or dissociated viral particles, preparation of organelle specific protein, nuclear or total cellular lysates of normal, transformed or malignant cells. Preferably, the purified protein has been prepared with ribohomopolymer chromatography as taught by (Swanson and Dreyfuss, 1993 and Matunis, 1994). Preferably, the purified protein is devoid of RNases.

The method further comprises the step of imposing binding conditions on the sample potentially containing target RNA-binding proteins in the presence of the first and second RNA libraries. RNA binding proteins exhibit different specificities and affinities for different RNA sequences. The imposition of binding conditions comprise the preparation of a master reaction mixture with both RNA libraries and the sample in the presence of 10 mM Tris-HCl (pH 7.4) and 2.5 mM $MgCl_2$. The reaction master mixture is divided onto four aliquots, each in a separate tube. The NaCl concentration is adjusted in one tube to 0.1M, in another tube to 0.5M, in third tube to 1M and in the fourth tube to 2M. Heparin is added to each tube in a concentration of 1 mg/ml to reduce nonspecific binding between protein and RNA and serve as a nuclease inhibitor. Preferably, each aliquot contains 2 mg of the purified, partially purified or unfractionated lysate protein. The reaction mixtures of each aliquot are incubated for 10 min at 4° C., after which the protein fraction is precipitated and washed with appropriate salt concentration and heparin buffer four times.

In the presence of the appropriate RNA-binding protein, certain first and second RNA molecules will bind RNA-binding protein. Preferably, the sequences of bound sections B and E have conformational complexity with a high degree of molecular rigidity. Complexity is suggested by sections having secondary structural elements such as symmetrical and asymmetrical bulges, double-stranded hairpins and terminal loops. The elements of the secondary structure are recognized by the RBD of the RNA-binding protein and, preferably, by more than one independent consensus sequence during the RNP complex formation. Preferably, the RNA-binding protein can bind more than one first and second RNA molecules. More preferably, RNA-binding protein can simultaneously bind at least one first RNA molecule and at least one second RNA molecule. And, the first and second RNA molecules form a ternary complex with target RNA-binding protein. And, most preferably, the first RNA molecule and the second RNA molecule bind two different consensus sequences of the same RBD.

Preferably, the secondary structural elements of the first and second RNA molecules exhibit a high degree of stability. That is, the structural elements are present under conditions in which the RNA is combined with the protein component. Such stable structures are kinetically favored and assure consistent folding of the RNA. RNAs having stable structural elements will form ternary complexes with the RNA-binding protein in a consistent efficient manner.

Preferably, the consensus sequences of RBD(s) regions are closely situated in RNA binding protein. The distance between the consensus sequences should be capable of being spanned by the sections C and D of the first RNA molecule and the second RNA molecule respectively. Preferably, the sections C and D comprise sufficient nucleotides to span the distance between the sections B and E as such sections B and E are bound to the RNA-binding protein. The terminal sequences selected for the sections C and D are capable of being ligated as the sections B and E are bound to the RNA-binding protein. The sections C and D may comprise random sequences selected for such sequences lack of affinity to the RNA-binding protein and inertness to other sequences of the first and second RNA library molecules.

Preferably, the sequences of sections C and D are capable of being ligated by RNA ligase. Alternatively, the sequences of sections C and D are capable of recognition by a ribozyme or incorporate ribozyme sequences. The sections C and D may comprise cloning sites required for the synthesis of the first and the second RNAs and cloning sites required to form a divided template sequence for the sections A and F. Bound to the RNA-binding protein and in the presence of ligating conditions, the sections C and D are ligated to form the third RNA molecule, which is an active template for a replicase enzyme. Preferably, the section C and D do not align contiguously with each another on the RNA-binding protein forming a gap between 20 and 200 angstroms. In forming the third RNA molecule several nucleotides of section C or D may be cleaved. Conditions for ligating RNA with RNA ligase and with ribozymes are known in the art.

Preferably, sections C and D are the nucleotide sequences, termed captomers, in the sense of acceptors and donors. As described, section C naturally terminates in the hydroxyl group required for ligation, and can act as a donor. Section D can serve as an acceptor, with a terminal monophosphate group required by the ligation reaction catalyzed by RNA ligase. A preferred RNA ligase is bacteriophage T4 RNA ligase. The ligation reactions are performed under standard conditions known to those skilled in the field of molecular biology.

A preferred sequence for section C is GGG as terminal transcriptional nucleotides after Eco RI digestion of the first recombinant plasmid library. A preferred sequence for section D is GGG as initial RNA transcriptional nucleotides of the second recombinant plasmid library.

Most of RNP proteins have a modular structure with one or more RNA-binding domain (RBD). RBDs in RNA-binding proteins are separated each from another. Each RBD generally exhibits more than one consensus sequence. Consensus sequences are normally separated, each from another, by stretches of approximately thirty amino acids. Preferably, the two consensus sequences of the RNA-binding protein exhibit an affinity to different nucleotide sequences, which are presented on at least one first RNA molecule and one second RNA molecule of the RNA libraries. The first and second RNA molecules from the first and second RNA libraries will simultaneously bind to two or more different consensus sequences. Structural elements of RBD provide an exposed surface that can serve as a platform to which RNA binds. Preferably, the bound RNAs remain exposed, as opposed to buried in a binding pocket. Therefore, the bound RNA molecules are accessible to other RNA processing factors, such as RNA ligase.

The method further comprises the step of imposing RNA ligase reaction conditions on the sample to form a third, hybrid, RNA molecule in the presence of the RNA-binding protein. The third RNA molecule is amplifiable by Q-beta replicase having both parts of the templates. The third RNA molecule has the formula:

5'-A-B-C-D-E-F-3'.

The optimal physical distance between the donor and acceptor parts of a first and second RNA molecule is approximately 1 to 50 nucleotides, more preferably, 5 to 25 nucleotides, and, most preferably, a distance of 10 to 16 nucleotides (Kaufmann et al., 1974, Sugino et al., 1977). RNA ligase aligns the free ends of the reacting donor and acceptor on its surface (Engler and Richarson, 1982, Uhlenbeck and Gumport, 1982) and catalyzes the formation of a 3'→5' phosphodiester bond between a 3'-terminal hydroxyl and a 5'-terminal phosphate of polyribonucleotide with the hydrolysis of ATP to AMP and Ppi (Silber et al., 1972).

As used herein, "RNA ligase reaction conditions" refers to conditions in which RNA molecules are ligated. Such conditions are known in the art and comprise, by way of example without limitation, the presence of an enzyme, such as RNA ligase, and suitable pH, temperature and the like.

Preferrably the third RNA molecule has a full length of MDV-I RNA sequence composed of 230 nucleotides (nt) set forth as SEQ ID No 5.

SEQ ID No 5
5'-GGGGACCCCC CCGGAAGGGG GGGACGAGGU GCGGGCACCU CGUACGGGAG UUCGACCGUG ACGCUCUAGA GAUCUAGAGC ACGGGCUAGC GCUUUCGCGC UCUCCCAGGU GACGCCUCGU GAAGAGGCGC GACCUUCGUG CGUUUCGGUG ACGCACGAGA ACCGCCACGC UGCUUCGCAG CGUGGCUCCU UCGCGCAGCC CGCUGCGCGA GGUGACCCCC GAAGGGGGGU UCCC-3'

Preferably, the method comprises the step of separating the unbound first and second RNA molecules of the first and the second RNA libraries from the third RNA molecules formed after RNA ligase reaction conditions are imposed. Preferably, the step of separating the unbound RNA molecules is performed by subjecting the sample potentially containing bound and unbound RNA molecules to filtration through nitrocellulose membrane filters. A preferred filtration procedure is as described by Giver et al., 1993. Briefly, the mixture containing the sample comprising RNA binding protein, non-bound to RNA-binding proteins first and second type RNA molecules, bound and non-ligated first and second type RNA molecules, and bound and ligated in various combinations first and second type RNA molecules (different third RNA molecules) is equilibrated at room temperature in the binding buffer. This mixture is vacuum filtered on HAW1P nitrocellulose filters (Millipore, Bedford, Mass.) using a pressure 5 1(0 inches of Hg. The filters are washed twice with excess binding buffer.

However, the separation step can be omitted and the third RNA molecules identified as an amplification product. In the event the separation step is omitted, the desired third molecule may be identified by it presence in quantities exceeding the unamplified first and second RNA molecules. With serial dilutions and multiple amplifications, the most common third RNA molecules are identified without any separation.

In order to proceed to the amplification step, the RNA bound to RNA-binding protein, including third RNA molecules are released from the RNA-binding proteins. Preferably, the hybrid RNA molecules are eluted from nitrocellulose filters using freshly made solution containing 200 ml of 7M Urea, 20 mM sodium citrate (pH 5.0), 1 mM EDTA solution combined with 500 ul of phenol, equilibrated with 0.1 sodium acetate pH5.2. The eluted solution of the third RNA molecules is extracted with ether, ethanol precipitated and the precipitate is resuspended in water (Giver et al., 1993). A number of different buffer conditions for elution of third RNA molecules bound to RNA-binding protein from the filters are known to the art, such as quanidinium chloride or thiocyanate.

Preferably, the signal moiety is sections A and F of the third RNA molecule, which sections allow recognition and replication by RNA replicase. Thus, the method further comprises the step of imposing RNA replicase conditions on the sample potentially comprising the hybrid, third RNA molecule. Preferably, the step of amplifying the third RNA molecules is performed in the presence of the enzyme Q-beta replicase. Reaction conditions for the enzyme Q-beta replicase are described by Axelrod et al., 1989.

The eluant, from the filter comprises non-ligated and ligated first and second type RNA molecules. Only third RNA molecules, that combine A and F segments, are amplifiable by Q-beta replicase. The sample is monitored for the presence of the third RNA molecule by its amplification by Q-beta replicase. The presence of hybrid, third RNA molecule is indicative of the presence of two RNA molecules bound to the RNA-binding protein. Preferably, at least one of the first or second RNA molecules has a signal moiety. As used herein, a signal moiety refers to a sequence, ligand, enzyme, or chemical entity capable of being detected. By way of example, without limitation, such ligand may comprise an antibody or antigen, biotin or avidin or streptavidin, or a sequence capable or binding to a probe or forming an reaction or amplification product. In the presence of the enzyme Q-beta replicase, sequences recognized by the enzyme generate an amplification product, which allows the sections A and F to act as a signal moiety. Preferably, the method further comprises the step of imposing RNA replicase conditions on the sample potentially comprising the hybrid third RNA molecule.

Once an amplified product has been obtained, the cDNA is synthesized in the presence of 5 Units of avian myeloblastosis virus and 2 uM reverse transcription primer complementary to 10–15 nucleotides of 3' of the hybrid RNA in the reaction conditions suggested by the vendor. The cDNA is cloned into an appropriate vector for sequencing. Sequencing of the individual clones determines the nucleotide composition of the third RNA molecule amplified by Q-beta replicase. The synthesis of cDNA for the third RNA molecules, using reverse transcriptase, cloning of cDNA in an appropriate vector and subsequent sequencing of cDNA clones corresponding to the third RNA molecules is within the skill individuals skilled in the art. The sequences of the first and second RNA molecules are deduced from the obtained sequences of the third RNA molecule and their secondary structures arc visualized using one of the commercially available computer programs.

A further embodiment of the present invention comprises a method for the construction of the first and the second RNA molecules with known nucleotide sequences. The first and second RNA molecules will be directly transcribed from machine-synthesized first complementary DNA (cDNA) encoding the first RNA molecule and a machine synthesized second cDNA encoding the second RNA molecule.

The composition of the first cDNA representing the first recombinant RNA is:

5'-L-Q I -O-P-3'

And, the composition of the second cDNA representing the second recombinant RNA is:

5'-L-M-R-Q2-3'

Wherein the sections represented by the letters L, M, O, Q1, Q2, P, and R are as previously described.

The organization and composition of the first recombinant RNA transcribed from the first synthesized cDNA molecules using T7 RNA promoter and T7 RNA polymerase is:

5'-A-B-C-3'.

And, the organization and composition of the recombinant RNA transcribed from the second cDNA using T7 RNA promoter and T7 RNA polymerase is:

5'-D-E-F-3'.

The letters A, B, C. D, E, and F are as previously described. These two recombinant RNA transcripts are the first and the second RNA molecules.

The nucleotide sequences of the regions and domains of sections B and and E of the first and second RNA molecules can be modified. Nucleotides may be added, subtracted and/or substituted. By way of example, without limitation, the sequences defining stems may be moved from one half of the stem to the other. The modifications may be designed by computer modeling techniques or by random mutations to the sequences. Modifications are made which allow each section with such sequence to bind to the target analyte in its specific consensus sequences, to be ligated by RNA ligase into one functional molecule, and to be a template that could be amplified by Q-beta replicase after its ligation by RNA ligase.

Preferably, modifications, including nucleotide substitutions, deletions and insertions are introduced into the nucleotide sequence of selected for sections B and E which increase the binding affinity, promote a particular original secondary structure, or facilitate the manufacture or synthesis of the RNA. Sections comprising B and E may require the insertion of cloning sites or retain other artifacts of synthesis. These modifications can be assessed by computer modeling techniques and empirical evaluation. Sections B and E, preferably, bind to the consensus sequences of RBD of the RNA-binding protein at physiologically normal conditions of pH, temperature, and ionic strength. Buffers for imposing such conditions are known in the art. Buffers, conditions, methods and procedures which are referred herein as being known in the art are described in Sambrook et al., (1989) and other references.

A further embodiment of the present invention features a method of determining the presence or absence of an RNA-binding protein molecule in a sample. As used herein, the term "sample" means a portion which is representative of the whole. The term includes biopsy material, clinical samples, forensic samples, sputum, saliva, blood and any other material in which the RNA-binding protein may be found.

The method comprises the steps of providing a first RNA molecule and a second RNA molecule. The first RNA molecule is capable of binding to a RNA-binding protein and has the formula

5'-A-B-C-3'.

The sections A, B and C are as previously described. The second RNA molecule is capable of binding to a RNA-binding protein and has the formula:

5'-D-E-F-3'.

The sections D, E and F are as previously described. The method further comprises the step of imposing binding conditions on a sample potentially containing RNA-binding protein molecules in the presence of the first and second RNA molecules. In the presence of the RNA-binding protein molecule, the first and the second RNA molecules form a ternary complex with such RNA-binding protein molecule. The method further comprises the step of imposing RNA ligase reaction conditions on the sample to form a hybrid, third RNA molecule in the presence of the RNA-binding protein molecule. The third RNA molecule has the formula:

5'-A-B-C-D-E-F-3'.

The sample is monitored for the presence of the hybrid RNA molecule, the presence or absence of which is indicative of the presence or absence of the RNA-binding protein molecule.

Preferably, at least one of the first or second RNA molecules has a signal moiety. The sections A and F, in the presence of the enzyme Q-beta replicase, are recognized by the enzyme and generate an amplification product. This amplification product can be readily detected with intercalating compounds such as propidium iodide and can act as a signal moiety.

A further embodiment of the present invention comprises a kit for determining the presence or absence of an RNA-binding protein molecule. The kit comprises one or more reagents comprising a first RNA molecule and a second RNA molecule. The first RNA molecule has the formula:

5'-A-B-C-3'.

The second RNA molecule has the formula:

5'-D-E-F-3'.

In the presence of the RNA-binding protein with affinity to the first and the second RNA molecules, the first and the second RNA molecules are capable of forming a protein-first-and-second-RNA ternary complex and in the presence of RNA ligase means forming a hybrid RNA molecule having the formula:

5'-A-B-C-D-E-F-3'.

The letters A, B, C. D, E, and F are as previously described. The hybrid RNA molecule is preferably capable of being received and replicated by RNA replicase.

Figure 3:
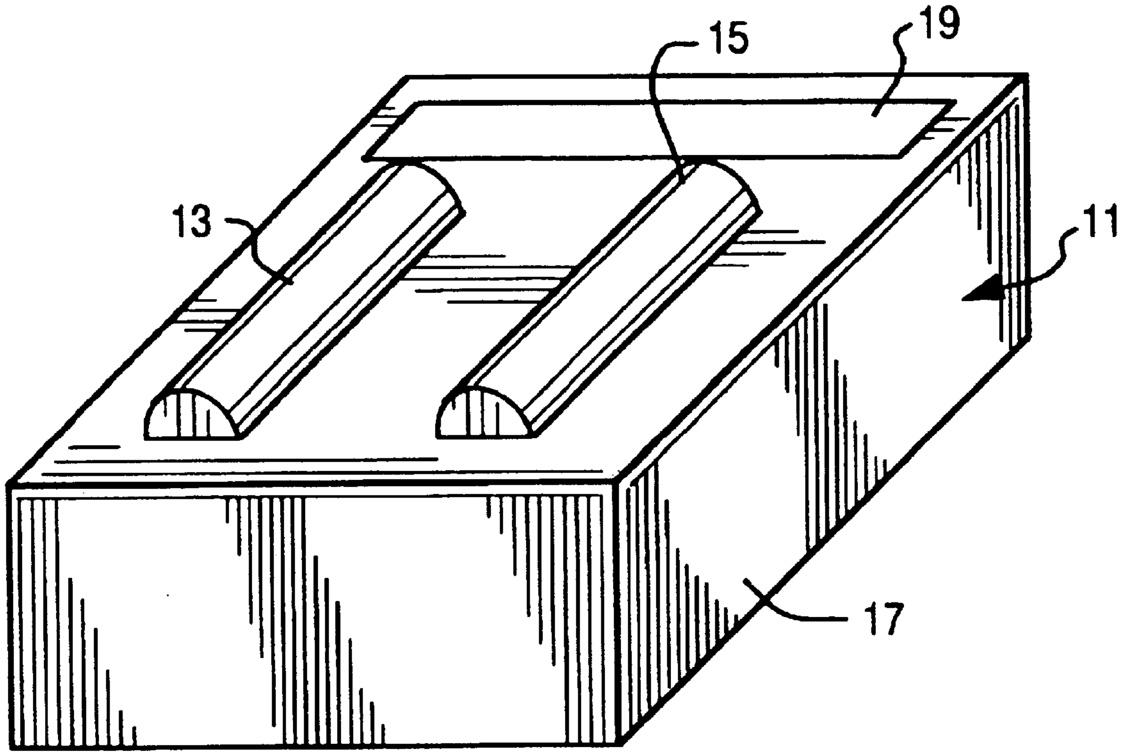
FIG. 3 depicts a kit embodying features of the present invention.

Preferably, the kit further comprises other reagents, such as, Q-beta replicase, RNA ligase, reverse transcriptase enzymes, suitable primers, buffers, intercalating agents and the like. Preferably, the kit comprises a DNA or RNA library. As used herein the term "kit" refers to an assembly of parts, compositions and reagents with suitable packaging materials and instructions. FIG. 3 depicts a kit, generally designated by the numeral 11, having features of the present invention. Kit 11 has a first vial 13 containing the first RNA molecule and a second vial 15 containing the second RNA molecule. In the alternative, the vials may contain one or more DNAs encoding such RNAs. Preferably, the kit 11 comprises a third vial (not shown) containing one or more DNA and/or RNA libraries. The kit 11 may also comprise other vials or containment vessels (not shown) containing enzymes, buffers, primers and reagents to facilitate the performance of the methods described herein. Preferably, the kit 11 comprises suitable packaging material, such as box 17, and instructions 19 outlining the methods of the present invention.

EXAMPLE 1.

Example 1 describes embodiments of the present invention in which adenovirus nucleic acid is used as a model for the RNA-binding protein. Using the above-cited specifics in the RNA ligase action, an experiment was performed in which a first RNA molecule and a second RNA molecule, with sections C and D, captomers, formed a 'loose' ternary complex with a nucleic acid target. This loose ternary complex resembles the complex formed by the first RNA molecule and second RNA molecule with a protein target. The example also highlights the ability of T4 RNA ligase to use such a model complex as a substrate and to restore a template for Q-bcta replicase by joining sections C and D of the first and second RNA molecules.

Preparation of the detector probes.

The fifty-base oligonucleotide sequence, SEQ ID No. 6, set forth below, was selected as a model target.

```
  1         10        20         30         40       50
5'-CGCGTTCGTCCTCACTCTCTTCCGCATCGCTGTCTGCGAGGGCCAGGGCC-3'
  I<----------------->I  I<--------------------->I
    Oligo #3 and #4             Oligo #1 and #2
```

The oligonucleotide sequence contains an Hha I-Pvu II region of the late promoter of adenovirus within map units 16.4 and 16.6 (Ziff and Evans, 1978). It was synthesized on a DNA Synthesizer, together with two pairs of oligonucleotides—oligos #1 (SEQ ID No. 7) and #2 (SEQ ID No. 8) and oligos #3 (SEQ ID No. 9) and #4 (SEQ ID No 10).

The first pair of oligos complement each other and represent the counterparts of the adenovirus target region from the nucleotide $C^{25}$ to the 3'-end of the sequence.

```
          XhoI       10          20         30    37
 Oligo    5'-TCGAGGCCCTGGCCCTCGCAGACAGCGATGAGCTCCC-3'
 #1
 Oligo        3'-CCGGGACCGGGAGCGTCTGTCGCTACTCGAGGG-5'
 #2             33  30        20         10   SacI SmaI
                                             (SstI)
```

Both oligos have additional sequences representing the complete site for Sac I and a half for Sma I restriction enzymes, and the oligo #1 additionally has a sequence of the Xho I restriction enzyme.

Oligos #3 and #4 represent the other half of the adenovirus target molecule and span from the 5'-beginning of the target sequence to the $T^{21}$ base.

```
              PpuM-1      10        2022
Oligo #3      5'-AAGAGAGTGAGGACGAACGCGC-3'

Oligo #4      3'-TTCTCTCACTCCTGCTTGCGCGAGCT-5'
                26     20        10     Xho I
```

Both oligos #3 and #4 have half of the recognition site for the PpuM-I restriction site and oligo #4 has a sequence of Xho I restriction enzyme, similar to oligo #1. These two pairs of oligos were also annealed and were used for cloning. These two pairs of oligos formed two dsDNA fragments, referred to as the 'PX fragment' and 'XS fragment'. These oligos were used for cloning in the recombinant plasmid pT7 MDV-XhoI.

Turning now to FIG. 2, this figure depicts plasmid pT7 MDV-XhoI. This plasmid was used for cloning of the synthesized PX and XS dsDNAs and for the transcription of the PX and XS recombinant RNA molecules that served as first and second RNA molecules for the adenovirus sequences. This plasmid is a variant of the parent plasmid, pT7 MDV, in which the XhoI linker sequence is not present. For further details of the construction of the vector, see Axelrod et al., 1991.

The pT7MDV-Xho I plasmid DNA was digested either with Ppu MI and Xho I or with Sma I and Xho I restriction enzymes and purified from the excised 65 bp or 166 bp fragments of the cloned MDV cDNA insert. The remaining parts of the pT7MDV-XhoI plasmid after Ppu MI and Xho I digestion (pT7 MDV-1) contained the T7 promoter and 168 bp 3' end of the MDV cDNA. The remaining part of the pT7MDV-Xho I plasmid digested with Xho I and Sma I enzymes (pT7 MDV-2) contained T7 promoter and the 62 bp 5' end of the MDV cDNA. The PX fragment was ligated with the pT7 MDV-1 and the XS fragment was ligated with pT7 MDV-2, forming pPX and pXS recombinant plasmids. The presence of the two different cloning sites in the digested vector ensures only one possible orientation of the inserts in both the pPX and pXS plasmids. Each of these plasmids contains a T7RNA promoter, an insert homologous to part of the target adenovirus sequence, and a segment of the MDV cDNA.

A control recombinant plasmid with target adenovirus DNA insert was constructed as well. For this purpose, we modified the original adenovirus sequence so that it contained Xho I sites at both ends similarly to PX and XS fragments. The fragment was then inserted at the Xho I site of pT7 MDV-Xho I, creating plasmid p325. This plasmid was used either to produce the DNA target sequences or to synthesize the recombinant template MDV RNA with an insert of the adenovirus sequences.

Cold or $^{32}P$-labeled RNA was transcribed from plasmids using T7RNA promoter after the Sma I digestion of pPX or p325 and Sst I or Sma I of pXS digestion according to the standard protocols (Sambrook et al., 1989)

The 193-base RNA transcript (SEQ ID No. 1) from the pPX plasmid is composed of (reading in the 5'→3' direction) the first three G residues of transcription initiation, 22 residues transcribed from the PX fragment and 168 residues transcribed from the 3' end of the MDV cDNA.

SEQ ID No. 11

5'-GGG-AAGAGAGUGAGGACGAACGCGC-3' MDV-1 RNA (168 bases).

The RNA transcript from the pXS plasmid (SEQ ID No. 12) is only 92 bases, shorter than the pT7MDV-1 transcript, and it starts with the 62 residues of the 5' end MDV cDNA and is followed by the 30 residues transcribed from the XS fragment.

SEQ ID No. 12

5'-MDV-1 RNA (62 bases)-GGCCCUGGCCCUCGCAGACAGCGAUGAGCU-3'.

An additional three C nucleotides were generated on 3' end of the XS recombinant RNA after Sma I digestion of the same plasmid.

These two recombinant RNAs represent a set of the first and second, PX and XS, detector RNA molecules. Each of these molecules has three functional parts: amplification, recognition and ligation.

Annealing experiments

PX detector was $^{32}p$ end-labeled to monitor the results of the annealing experiments. For this we used bacterial alkaline phosphatase (BAP) and bacteriophage T4 polynucleotide kinase. Both reactions, dephosphorylation and end-labeling, were performed according to standard protocols (Sambrook et al., 1989). Incorporation of the radioactive label was measured in aliquots of the reaction and the percentages of incorporation were calculated.

The annealing reaction products between the PX and XS detector-molecules and adenovirus target sequences were characterized. The annealing reaction was performed with PX and XS RNAs but without adenovirus target molecules. Three separate annealing reactions with PX, XS and adenovirus target molecules were performed. PX recombinant RNA was $^{32}$p end-labeled using standard methods. Annealing was achieved by boiling the reaction mix two minutes and then incubating it at 65° C. for two hours. The annealing reaction was carried out in a solution containing 50 mM TRIS pH 7.8, 5 mM $MgCl_2$, 0.5 mM ATP and 1 mM EDTA, 10% non-denaturing PAGE at 500 volts for eight hours.

Several bands in a range from 300 nt to 190 nt were seen on autoradiographs. The most plausible explanation of the results is that the 300 nt band results from the annealing of the target DNA molecule with both RNAs. Such complex is composed of from 50 bp double stranded heteroduplex of target/probes segment and 168 bases 3'-end and 62 bases 5'-end of MDV-1. The lowest band is 193 nucleotides of non-hybridized PX RNA and one of the middle bands, with a size of 243 bases, is a complex between PX RNA and adenovirus DNA molecules. The origin of the second band of similar size is unknown.

The efficiency of hybridization was calculated as a percentage of the radioactivity of the top band from the total radioactivity applied on the gel. Usually more than 50% of the total number of PX RNA molecules participate in hybridization with the adenovirus target molecule by itself or in compound with XS. The yield of the ternary complex formed by two RNA detector molecules and the target molecules was, usually, close to 30–40%.

The diagram below illustrates a possible hybridization configuration between the target adenovirus sequence (SEQ ID No. 13), and the two RNA transcripts. The SX RNA detector in this case, was generated by Sst I digestion of the pSX plasmid.

SEQ ID No. 13

```
  1        10         20   24     30         40       50
  CGCGTTCGTCCTCACTCTCTTCC-G-CATCGCTGTCTGCGAGGGCCAGGGCC

H GCGCAAGCAGGAGUGAGAGAAGGJGUAGCGACAGACGCUCCCGGUCCCGGI
|      PX detector molecule        XS detector molecule
```

As used above with respect to the ligated detector molecules (SEQ ID No. 14), the letter J represents a loop of unhybridized nucleotides in a sequence of 3'-GUCGA-5', which separate the PX and XS detector molecule sections. The letter H represents 168 bases of MDV-1 RNA-3'. And, the letter I represents 62 bases of MDV-1 RNA-5'. There is complete complementarity along the PX RNA detector and the first 23 bases of the target molecule, but not the last, the $24^{th}$ G-residue of the transcript and the G-base of the adenovirus target molecule. The first four bases of the XS detector (UCGA) do not have homologous nucleotides on the target DNA molecule, although the rest of the transcript is complementary to the target molecule. Thus, the hybridized RNA transcripts do not juxtapose to the target, in end-to-end fashion, but rather leave a ~20 Angstrom gap between the terminal hybridized nucleotides.

The G and UCGA nucleotides of the PX and XS detector probes are the the sections C and D, captomers, of the first and second RNA molecules. They do not hybridize to the target and comprise structures similar to the donor/acceptor complex, which is necessary in order for RNA ligasc to form a phosphodiester bond (Uhlenbeck, 1983). The G captomer is a donor with a 5'-phosphate terminus and the UCGA captomer is an acceptor with a 3'-hydroxyl terminal group on the U residue.

Ligation experiments

The recombinant plasmid pXS was constructed in a manner that it could be linearized either with Smal or SstI for RNA transcription (See Diagram above). The two XS RNA detector molecules are different in the total lengths and composition of their captomers. The XS detector generated with Sst I digestion had a captomer of four UCGA-base-long bases, whereas the captomer generated after the Sma I digestion was longer for the three Cs.

Ligation reactions were carried out on 4 ul aliquots taken directly from the annealing reactions in the presence of the 1 OnM mercaptoethanol, and 40 Units of T4 RNA ligase at 25° C. after confirmation by gel electrophoresis that hybridization was successful. The duration of the reaction varied from 2 hours to overnight. The bands representing ligation products composed of PX-SX ligated detector molecules were excited and their radioactivity was measured and compared with the total radioactivity of the aliquot from the annealing reaction used for the ligation.

Several bands, with a maximal band of approximately 300 nt were seen on the autoradiographs of the electrophoresed products after the ligation reaction. Products of the ligation reaction and non-ligated PX transcripts were seen on the autoradiographs. The products of the annealing reactions, which were performed with PX and XS transcripts without the target adenovirus DNAs, served as a negative control. Only PX transcripts were seen compared with Control p325 RNA transcripts. The total volume of each ligation reaction was 10 ul, with the final concentrations 10 mM, 5 mM $MgCl_2$ and 2 Units of T4 RNA ligase in the presence of 20% PEG. The reaction was performed at 25° C. and ended by adding 1 ul of 100 mM EDTA, 7M Urea denatured 10% PAGE at 500 volts for eight hours of electrophoresis.

Additionally, the duration of the reaction apparently does not affect the rate of ligation when the long captomers were used. The yield of the ligated product was 20.0 % after two hours of reaction and 18.7% after overnight. The longer reaction time, however, might have a certain disadvantage when the short captomers are used. The overnight reaction yielded 18.4% compared with 33.2% after two hours of reaction. The reduction in the percentages of ligated products after a prolonged reaction time apparently indicates that the ligation products composed of PX and XS RNA transcripts are not stable and dissociate over time. The results of the ligation experiment demonstrates that the length of the XS captomer seemingly does not effect the ligation rate of the RNA transcripts, although the highest ligation rate was observed when the acceptor-captomer was composed of the seven-AGCUCCC-residues. $^{32}$P-labeled recombinant MDV-I RNA, with the adenovirus insert transcribed from the p325 plasmid, served as a reference marker.

TABLE 1

Effect of the captomer's length on the yield of the ligation products between PX and XS RNA transcripts. 4 ul aliquots of the annealing reactions (1–6*) with two RNA transcripts and adenovirus target DNA were used for the subsequent ligation reaction. 4 ul aliquots of the annealing reaction (7**) without the target DNA were used as the negative control.

| Test # | Length of captomer used in the reaction | Duration of reaction at 25° C. | Total counts (cpm) of the band in the gel | The proportion (%) from the counts loaded |
|---|---|---|---|---|
| 1. | Short[1] | 2 hours | 3428 | 20.0% |
| 2. | Short | o/n | 3140 | 18.7% |
| 3. | Long[2] | 2 hours | 5576 | 33.2% |
| 4. | Long | 2 hours | 1657 | 9.9% |
| 5. | Long | o/n | 3085 | 18.4% |
| 6. | Long | o/n | 1385 | 8.2% |
| 7. | Long | 2 hours | 98 | 0.01% |

*16.800 cpm were loaded into each test lane
**76.700 cpm were loaded into a control lane The short (UCGA) captomer was generated by the pXS plasmid DNA digestion by the Sst I restriction enzyme, and the long (AGCUCCC) captomer resulted from the digestion of the pXS plasmid DNA by the Sma I restriction enzyme.

The ligation product composed of the ligated PX and XS RNA detector molecules was purified by gel electrophoresis. The purified product was used as a template for Q-beta replicase.

Amplification of the ligation products by Q-beta replicase

Q-beta replicase reactions were carried out on a volume of 20 ul at 37° C. during 25–30 minutes in 50-ul reactions containing 88 mM Tris-HCL (pH 7.5), 12 mM Mg-$C_2$, 0.2 mM of each ribonucleoside triphosphate, 25 uCi of [alpha-$^{32}$P]GTP, 90 pm/ml of Q-beta replicase, and 11.2 pm/ml of template RNA. From this mixture, 7 to 15 ul was applied directly onto a denaturing polyacrylamide gel containing 7M Urea for electrophoretic analysis. Additionally, adsorbed radioactivity was determined by liquid scintillation.

The Q-beta replicase experiment demonstrates that there are no templates for Q-beta enzyme in the aliquots representing the tube in which the ligation was performed without the adenovirus target, which indicate that target analyte was necessary to unite two detector probes. A ligation reaction was performed on aliquots of the annealing reaction. The 5 ul aliquots from each reaction were analyzed on a non-denaturing gel. An aliquot from the annealing reaction without the adenovirus target sequences, with adenovirus sequence and without PEG, and in the presence of the target adenovirus sequences and PEG were compared to the Q-beta replicase products of pT7 MDV-XhoI plasmid as a control. The data indicated that amplification of the template by Q-beta replicase occurred only when ligation of the PX and XS RNA detector molecules took place in the presence of the target.

EXAMPLE 2.

Figure 4A:
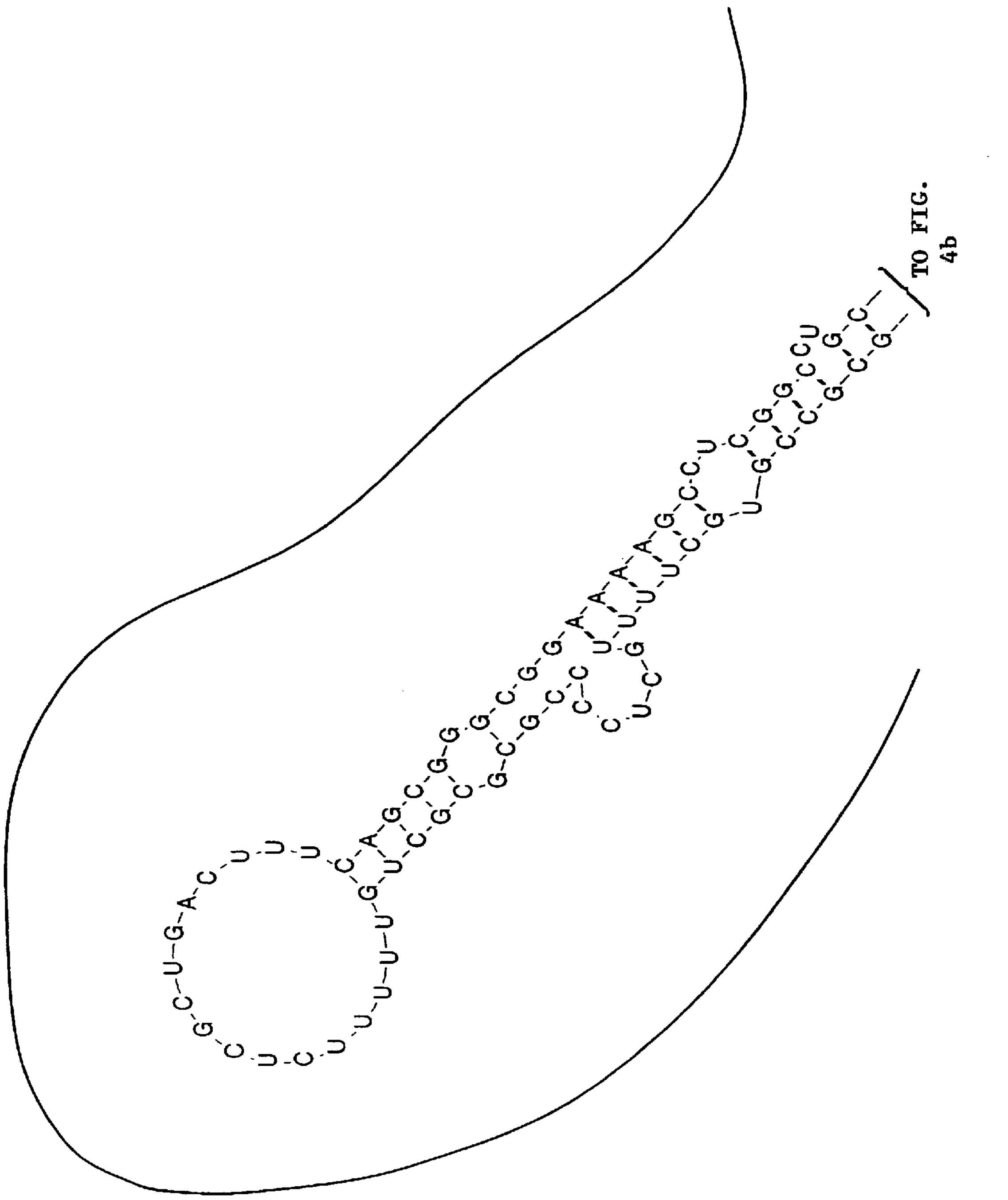
FIGS. 4*a* and 4*b* depicts a region, designated herein as the Y region, of hTR molecule.
Figure 4B:
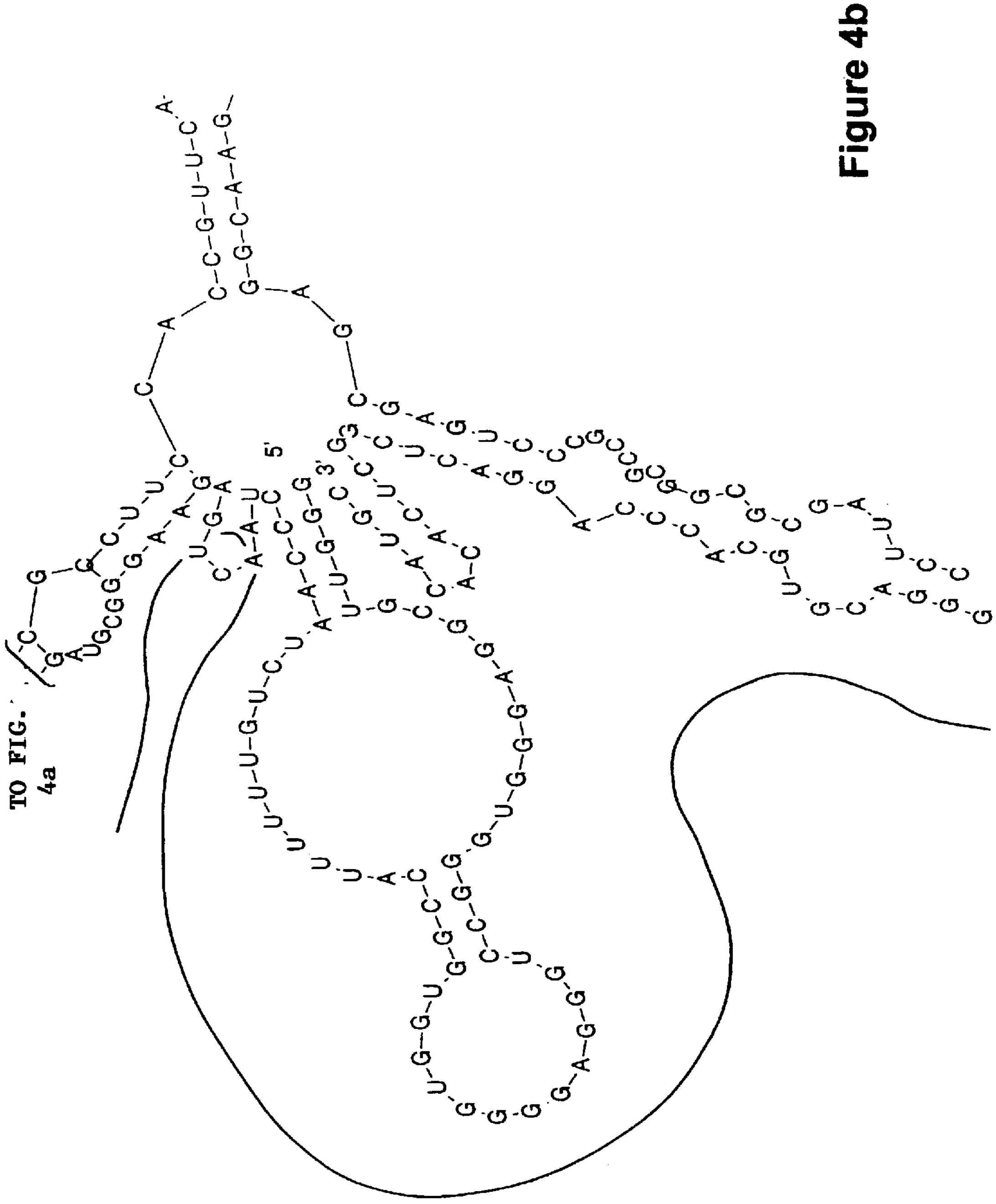

This Example features a first RNA molecule and a second RNA molecule, which are capable of binding to a RNA binding protein, the protein component of human telomerase. The first and second RNA molecules have sections B and E which have sequences of the Y-1 or Y-2 domains of human telomerase RNA component (hTR). These domains are situated near each another in hTR. The single stranded sequences with a section of the telomere's sequence spanning the two domains are used as the sections C and D, captomers. These captomer sequences comprise a donor and an acceptor accessible for T4 RNA ligase (FIGS. 4*a* and 4*b*).

A computer analysis of the secondary structures of the first and the second RNA molecules with the sections A and F comprising sequences of MDV-1 RNA template with section B and E comprising sequences of Y-1 and Y-2 suggest that the secondary structure of Y-1 and Y-2 domains remain intact. Thus, Y-1 and Y-2 sequences will be recognizable by the corresponding topological sites of the first subunit protein component after being incorporated into the recombinant RNA. A small modification (minideletions) will be introduced into the nucleotide sequence of the first detector molecule to protect the original secondary structure of the Y-1 segment without compromising the ability of the whole molecule to be ligated by RNA ligase and to be amplified by Q-beta replicase (FIG. 5*a*).

Figure 5A:
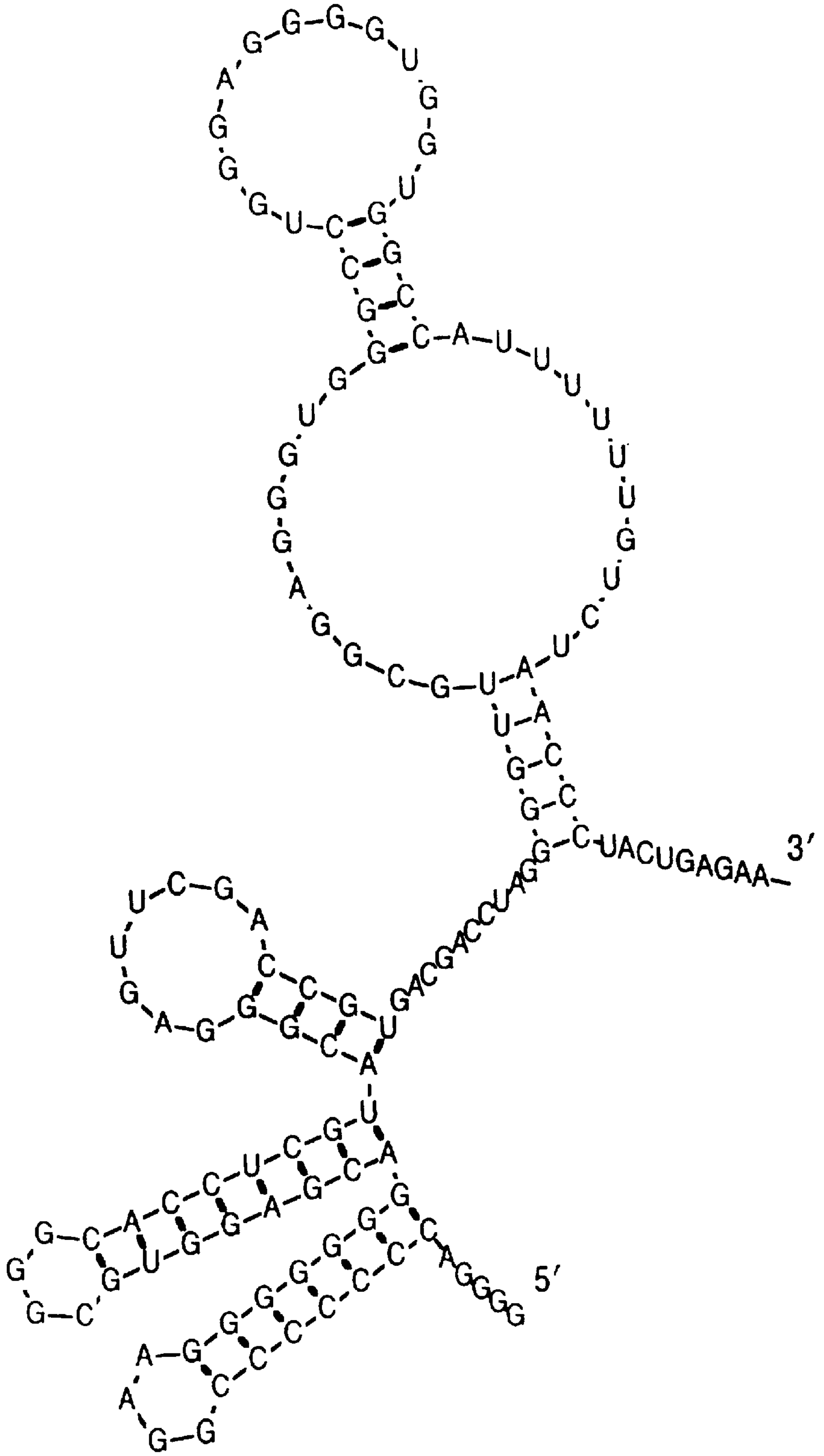
FIGS. 5*a*, 5*b* and 5*c* depict two recombinant RNAs.
Figures 5B, 5C:
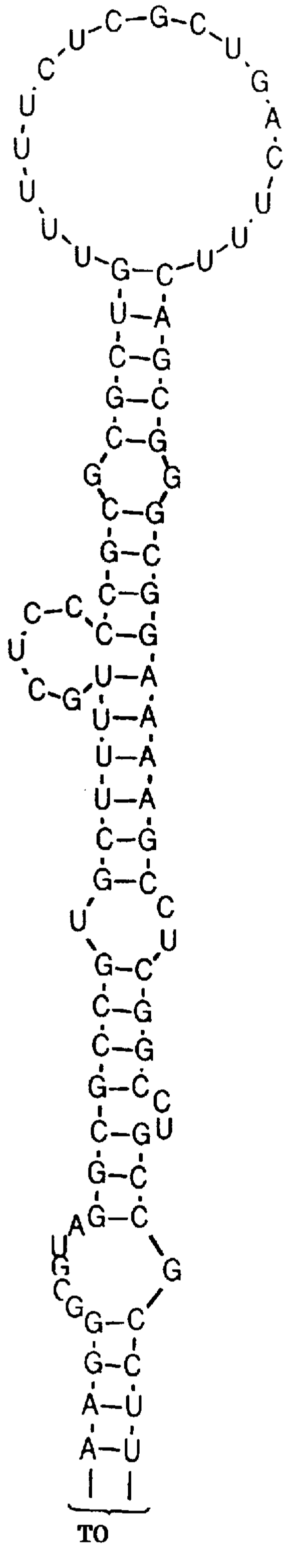
Figure 5C:
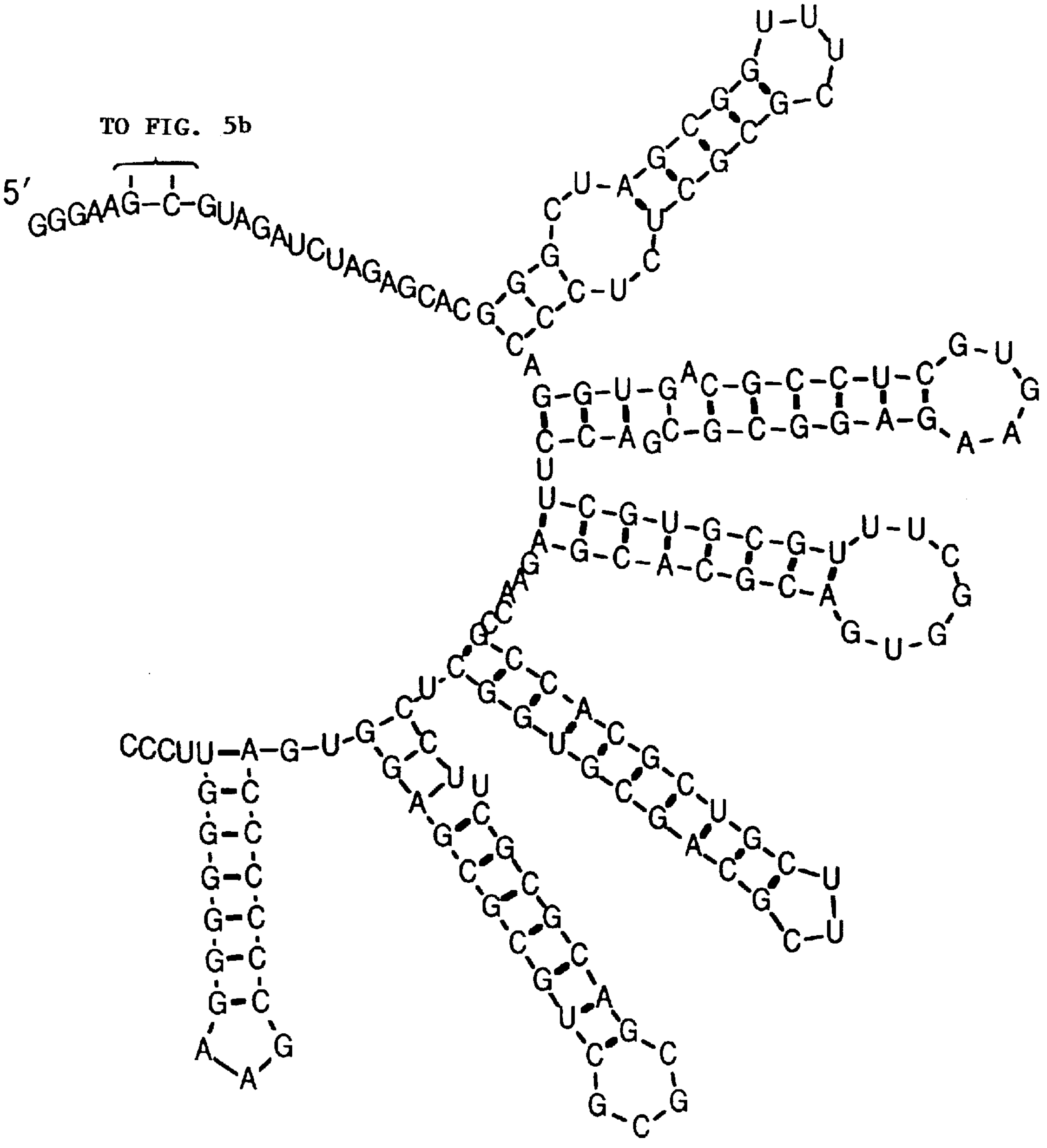

FIG. 5*a* depicts a recombinant RNA with Y-1 domain and Q1 (5' MDV-1 RNA) sequences. This structure conforms to sections A-B of the first RNA molecule. FIG. 5*b* depicts the Y-2 domain and Q2 (3' MDV-1 RNA) sequences. An adjustment, a deletion of a single cytosine nucleotide, show by an arrow, is made to keep the original secondary structures of the Y-1 domain. This structure conforms to the sections E-F of the second RNA molecule.

To construct first and second RNA molecules, two dsDNA will be synthesized. The first dsDNA will represent 58 nt of the Y-1 domain with terminal XhoI and Eco RI sites, and another dsDNA, will represent 91 nt of the Y-2 domain with terminal PpuI and XhoI sites. Such two dsDNAs will be cloned in a pT7 MDV-Xho I plasmid (FIG. 2), using the same strategy and procedures as was described in the above experiments with adenovirus sequences. The first dsDNA is described in sequences set forth below (SEQ ID No. 15 and SEQ ID No. 16).

SEQ ID Nos. 15 and 16

```
      XhoI
5'-TCGA-GGGGTTGCGGAGGGTGGGCCTGGGAGGGGTGGTGGCCATTTTT

        3'-CCCCAACGCCTCCCACCCGGACCCTCCCCACCACCGGTAAAAA

        TGTCTAACCCTACTGA-GAA-3'

        ACAGATTGGGATGACT-CTT5' EcoRI
```

The second ds DNA is described in the sequences set forth below (SEQ ID No. 17 and SEQ ID No. 18):

SEQ ID Nos. 17 and 18

```
PpuMI
5'-AA-
  GAAGGGCGTAGGCGCCGTGCTTTTGCTC-
  CCCGCGCGCTGTTTTT
3'-TT-
  CTTCCCGCATCCGCGGCACGAAAAC-
  GAGGGGCGCGCGACAAAAA
  CTCGCTGACTTTCAGCGGGCGGAAAAGC-
CTCGGCCTGCC              GCCTTCGT-3'
GAGCGACTGAAAGTCGCCCGCCTTTTCGGAGCCG-
GACGGCGGAAGCA-AGCT-5 XhoI
```

The recombinant plasmids for a synthesis of two recombinant RNA transcripts, composed of the hTR and Q-beta replicase template sequences, will be used similarly to those of the PX and XS for adenovirus, employing T7 RNA promoter and T7RNA polymerase.

The first 62 nt at the 5' end of the first recombinant RNA are 5'-terminal sequences of MDV-1 RNA. The MDV-1 sequence is followed by Y-1 domain sequences. A 10 nt sequence (CUAACCCUAC), a telomere's template sequence, should be modified by a single (A) nucleotide deletion to preserve a secondary structure of the Y-1 domain. The template sequences will be followed by the terminal 3 nt (UGA) of Y-1 hTR and a Eco RI restriction site sequence (GAA), which represents the donor captomer, naturally terminated with the hydroxyl group required for ligation. The second recombinant RNA is started with the transcriptional (GGG) and PpuMI (AA) nucleotides. These five nucleotides composed an acceptor captomer. It should follow by the sequences of C-2 domain and MDV-I RNA regions. The secondary structures of the two recombinant RNA are shown in FIGS. 5*a* 5*b* and 5*c*.

Normally after synthesis, the 5' end of the second recombinant molecule would contain a triphosphate group, which cannot participate in ligation. However, in addition of providing quanosine triphosphate as a precursor for transcription of the second recombinant RNA, a 20-fold excess of guanosine monophosphate should be provided. The monophosphate will be incorporated into the 5' termini, assuring that most second recombinant molecules will contain the monophosphate group required for ligation (Tyagi et al., 1996). Such procedures for substitution of triphosphate in the 5' termini should be omitted during a construction of the first recombinant RNA. This molecule will have triphosphate at the 5' termini, which prevents a ligation of 5' and 3' ends of MDV template.

EXAMPLE 3

This Example features a first and a second RNA molecule having sections B and E corresponding to domains Y-1 and Y-2, and sections A and F corresponding to sections of the nanovariant RNA template. A computer analysis of the secondary structures of the first and second detector molecules suggest that the secondary structure of Y-1 and Y-2 domains remain intact, similar to the first and second RNA molecules with MDV-1 RNA template of Example 2.

A oligonucleotide of 114 bases comprising T7 RNA promoter sequences followed by the 34 nucleotides of the 5'end nanovariant RNA and Y-1 hTR domain sequences will be synthesized. A ds DNA having such sequences is described below (SEQ ID No.19):

SEQ ID NO: 19

```
T7 RNA promoter      5' end nanovariant RNA
5'-ATTATGCTGAGTGATATCCC-CTTTAGGACAATGGTCCTATTGCCCCAAAGGAGA

Y-1 hTR domain
*CCCAACGCCTCCCACCCGGACCCTCCCCACCACCGGTAAAAAACAGATTGGGATG
ACT-3'
```

Another oligonucleotide of 165 bases comprising T7 RNA promoter followed by third hTR domain sequences and 54 nucleotides of 3'end nanovariant RNA sequences will be synthesized. A ds DNA having such sequences is described below (SEQ ID No. 20):

SEQ ID No. 20

```
  T7 RNA promoter           Y-2 hTR domain

5'-
ATTATGCTGAGTGATATCCCTTCCCGCATCCGCGGCACGAAAACGAGGGGCGCGC

GACAAAAAGAGCGACTGAAAGTCGCCCGCCTTTTCGGAGCCGGCGCCTTTTCGGAG

CCGG-

  3'end nanovariant RNA
CCAGAGATGACGTTTCAATCTCTCCTGTGTGGGCCTAGATCGGCCCAGTTGGGT-
3'
```

Figure 6A:
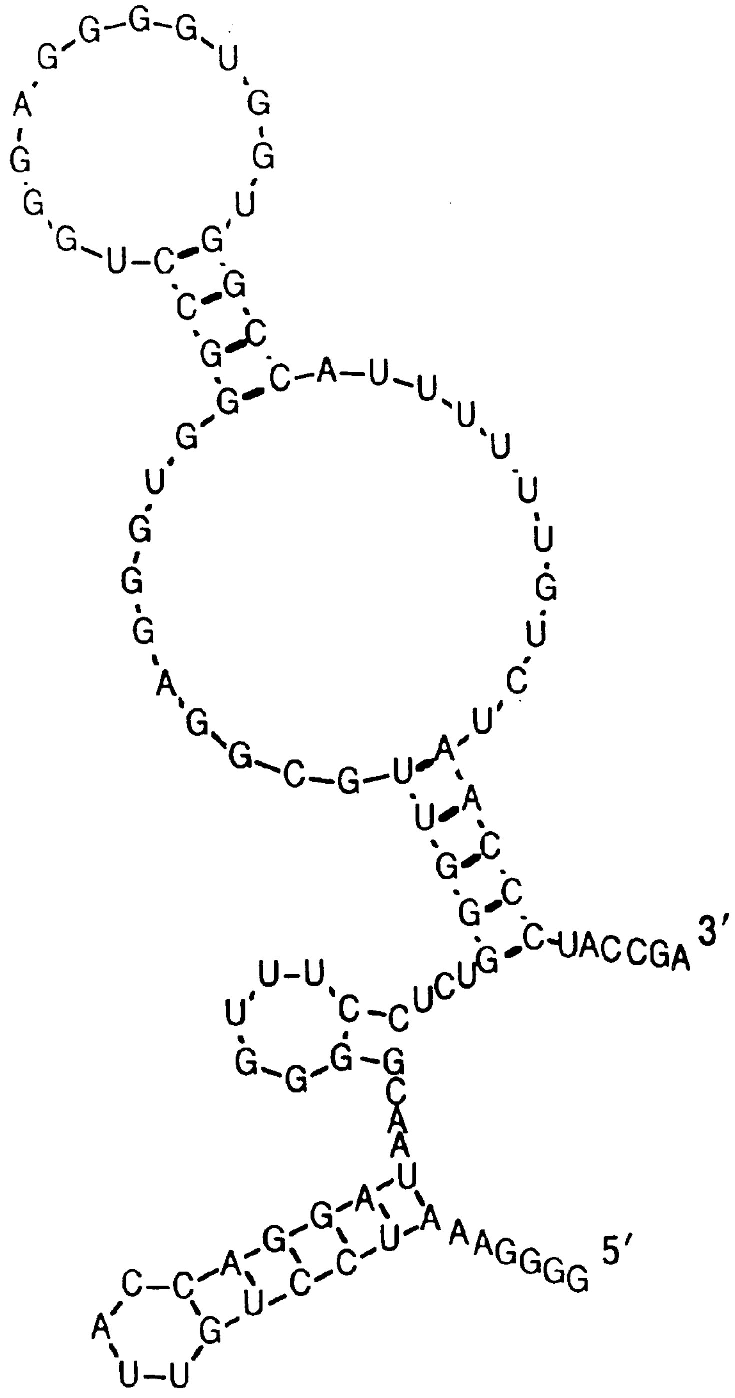
FIGS. 6*a* and 6*b* depict two recombinant RNAs.
Figure 6B:
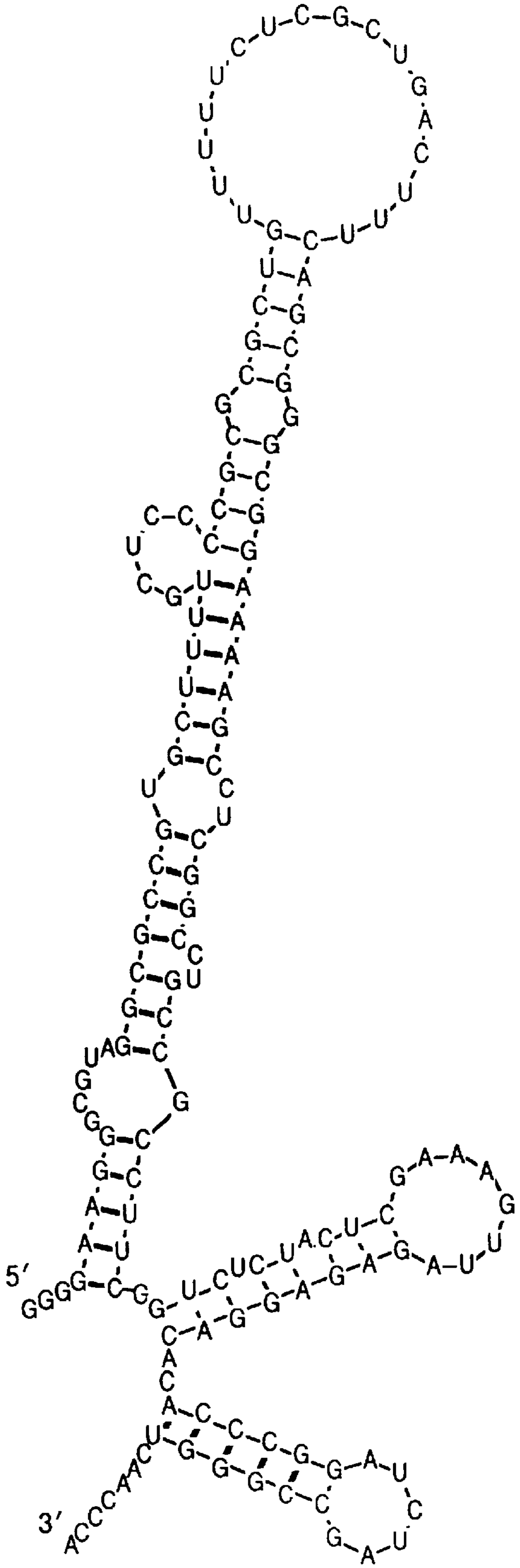

These two oligonucleotides will be used directly as templates to synthesize two recombinant detector RNA molecules composed hTR and nanovariant RNA sequences, using the standard procedures of in vitro RNA synthesis (Sambrook et al., 1989). The complete secondary structure of these two RNA molecules are shown in FIGS. 6*a* and 6*b*. The compositions of the recombinant RNA molecules with nanovariant RNA sequences is similar to those of MDV-I RNA, except that the donor captomer is composed of 6nt (UACCGA) and the acceptor captomer is composed of 3 nt (GGG).

Turning now to FIGS. 6*a* and 6*b* and, in particular, FIG. 6*a*, FIG. 6*a* depicts a recombinant RNA with Y-1 domain and Q1 (5' nanovariant RNA) sequences. This structure conforms to sections A-B of a further embodiment of a first RNA molecule. FIG. 6*b* depicts a recombinant RNA with Y-2 domain and Q2 (3' of nanovariant RNA) sequences. This structure conforms to the sections E-F of a further embodiment of a second RNA molecule.

The secondary structure of Y-1 domain and Y-2 domain sequences in the four recombinant RNAs have the same secondary structure as these domains in the native hTR. The single stranded spacers between hTR domain and Q-beta replicase sequences will provide flexibility for the Y-1 and Y-2 domains of the recombinant RNA molecules to bind to the first subunit protein component in the corresponding epitopes as Y-1 and Y-2 domains of the native hTR. Neither of the two recombinant RNA molecules can serve as a template for Q-beta replicase. However, the two recombinant RNA molecules of the particular set will form a functional template after binding with to the subunit and ligation by T4RNA ligase.

EXAMPLE 4

Example 4describes first and second detector molecules which are capable binding Rev protein of the human immunodeficiency type 1 virus (HIV-1). The central role of Rev protein in primary and reactivated HIV-1 infections is well studied. It is believed that Rev protein binds the Rev Responsive Element (RRE), a segment of specific structure within mRNAs. Rev protein participates in the transport of RRE from host nuclei to cytoplasm (Karn et al., 1991). The interaction of the Rev protein and the cis-acting Rev Responsive Element (RRE) is required for cytoplasmic accumulation of HIV structural proteins encoding viral mRNAs (Malim et al., 1989). Without Rev protein the gene transcripts fail to accumulate and the virus cannot replicate (Sodroski et al., 1986).

The structure of RRE and mechanism of its interaction and Rev protein as well as RRE aptamers with Rev protein are well studied (Karn et al., 1991). The RRE and its aptamers consist of three structural parts—one asymmetrical bulge, the binding element, termed core region, and two double stranded stems that flank the core region. Experiments with nucleotide substitution suggest that the annealing abilities of the whole RRE element or its aptamer depend on the existence of the core region, its nucleotide composition and on its spatial configuration. The nucleotide composition of the flanking stems is not crucial as long as they ensure the existence of the core region (Giver et al., 1993 a, b ). The nucleotides from $U^{45}$to $G^{53}$ and from $C^{65}$ to $A^{75}$ in the core region of Rev binding domain are involved in the binding motif for Rev recognition. A major groove is formed in the core region by the two G bases, underlined and in bold in the diagram below (Seq ID Nos. 21 and 22):

```
            G
       G       C G
5'-U 45G             CAG 53-3
3'-A 75C            GUC 65-5'
       AU      GCA
            G
```

These two G nucleotides open, or pull apart, the otherwise stringed stem of complementary nucleotides. Such widening is necessary for spatial positioning of the Rev peptide's 'epitopes' precisely in the major groove. Finally, hydrogen bonds form between the Rev protein and RNA that secure a tight and specific binding into the complex (Iwai et al., 1992).

Example 4 features a step of providing cDNA library constructed from RNA pool representing the cell infected with HIV-I virus and, preferably, a construction of cDNA from total, rather than a poly(A) RNA. The cDNA pool is subjected to the normalization to decrease the redundancy of abundant sequences characteristic to the host-human DNA and to increase a representation of the HIV specific RNA sequences. The original cDNA library is fragmented by mechanical shearing or by enzymatic digestion in a sequence non-specific manner to the average size of 30 to 100 nt using the methods referred previously (Gudkov et al., 1994).

Further, the normalized and fragmented cDNA library is divided into two parts and construction of the first and second recombinant RNA libraries are made to the protocols previously outlined and depicted in the FIGS. 1*a*–1*d*. The annealing and ligation for first and second recombinant RNA is performed in the presence of the purified Rev protein according to the protocols previously described and depicted in the FIGS. 1*e*–1*f*. The ligated recombinant RNA molecules are amplified using the standard methods for performing Q-beta reactions. The amplification product is used to synthesize the cDNA for further sequencing and for a deduction of the detector, B and E, parts and captomers, C and D, for each of the recombinant RNA molecule. The composition of the complex recombinant q-beta replicase template is represented below (Seq ID No 23).

Seq ID No. 23

5'-62ntMDV-(N)n-UGGGCGCAG-(N)n-AGCU-GGG-AA-(N)n-CUGACGGUACA-(N)n-168ntMDV-3'

The sections of the above molecule, 5'-UGGGCGCAG-3' and 5'-CUGACGGUACA-3', are the B and E parts that bind the RRE domain of the Rev protein. The section of the above molecule, AGCU and GGGAA, represent the aptamer segments, sections C and D, with 3' U and 5' G termini. These termini are ligated by T4 RNA ligase in a ligation reaction.

The manner that two recombinant RNA molecules will form a ternary complex with Rev protein is described below:

```
                          G
                        G   CG
5'--62ntMDV--(N)n-UG          CAG--(N)n--AGCU--3'
3'--168ntMDV--(N)n-AC         GUC--(N)n--AA-GGG-5'
                       AU GCA
                          G
```

The nucleotide composition of the two recombinant RNA molecules is presented below (Seq ID Nos. 24 and 25). The four 3' terminal nucleotides AGCU of the first recombinant RNA molecule represent Sacd restriction site used for transcription of the first recombinant plasmid library for a production of the first recombinant RNA library. Similarly, the five 5' terminal nucleotides of the second recombinant RNA molecule represent the first three transcription nucleotides , GGG, and the Ppu-MI restriction site, AA.

Seq ID Nos. 24 and 25

5'-62ntMDV-(N)n-UGGGCGCAG-(N)n-AGCU—3'

5'-GGG-AA-(N)n-CUGACGGUACA-(N)n-168ntMDV—3'

Thus, while preferred embodiments have been illustrated and describe, it is understood that the present invention is capable of variation and modification and, therefore, should not be limited to the precise details set forth, but should include such changes and alterations that fall within the purview of the following claims.

REFERENCES

PUBLICATIONS

Axelrod V A., Brown E., Priano C. and Mills D R. 1991. Virology, 184, 595–608

Dobkin C., Mills D R., Kramer F R. and Spiegelman S. 1979. Biochemistry 18,2038–2044.

Dreyfuss G., Matunis M. J., Pinol-Roma S. and Burd C. G. 1993. Annu. Rev. Biochem. 62, 289–321

Engler M J. and Richardson C C. 1982. The enzymes. Academic Press, Inc. vol XV. 3–29.

Giver L. Bartel D. Zapp M., Pawu A., Green M., and Ellingnton A D. 1993. Gene 137, 19–24

Gudkov et al, 1994

Kauftnann G., Klein T. and Littauer U Z. 1974. FEBS Lett. 46, 271–275.

Kiledjian M., BurdCG., Gorlach M., Portman D and Dreyfuss G. 1994. In Frontiers in Molecular Biology, 127–149.

MatunisM J., Matunis EC. and Dreyfuss G. 1994. Methods in Cell Biology, 44, 191–205.

Minushkin A V., Voronin L A., Ugarov V I., Bondareva L A., Chetverina H V and Chetverin A B. 1991. J. Mol. Biol. 221, 463–472.

PrianoC., Kramer F R. and Mills D R. 1987. Cold Spring Harbor Symp. Quant. Biol. 52, 321–330.

Patarjala et. al 1991.

Sambrook J., Fritsch E F and T. Maniatis. 1989. Molecular Cloning. Cold Spring Harbor Laboratory Press.

Silber R. Malathi V G. and Hurwitz J. 1972. Proc. Natl. Acad. Sci. USA 69, 3009–3013

Sugino A., Goodman H M., Heyneker H L., Shine J., Boyer H M. and Cozzarelli N R. 1977. J. Biol.Chem. 252, 3978–3987

Swanson M S and Dreyfuss G. 1993. Mol. Cel. Biol. 8, 2237–2241

Tyagi S., Landergen U., Tazi M., Lizardi P M. and Kramer FR. 1996. Proc. Natl. Acad. Sci. USA. 93, 5395–5400.

Uhlenbeck O C and Gumport R D. 1982. The enzymes. Academic Press, Inc. vol XV. 31–58.

Uhlenbeck O C. 1983. TIBS. March, 94–96.

Uhlenbeck O C. 1987. Nature 328, 596–600

Weissmann C., Feix G. and Slor H. 1968. Cold Spring Harbor Symp. Quant. Biol. 33, 83–100

Ziff E B. and Evans R M. 1978. Cell 15, 1463–1475.

What is claimed is:

1. A first ribonucleic acid (RNA) molecule and a second RNA molecule for use in binding an RNA-binding protein having a protein component and a RNA component, said first RNA molecule capable of binding to said RNA-binding protein and having the following formula:

5'-A-B-C-3';

wherein A is a section of the RNA molecule having 10–100,000 nucleotides which section is capable of being received by an RNA replicase and with another RNA sequence, F, being replicated, the letter "B" denotes a section of the RNA molecule having approximately 10 to 3,000 nucleotides which have affinity to one consensus sequence of said RNA-binding protein and which are capable of binding to said protein component, and the letter "C" denotes a section of the RNA molecule having approximately 1 to 20 nucleotides which section is capable of being ligated to another RNA sequence, "D" of the second RNA molecule: the second RNA molecule capable of binding to said RNA-binding protein and having the following formula:

5'-D-E-F-3';

wherein D is a section of the RNA molecule having approximately 1 to 20 nucleotides which section is capable being ligated with another RNA sequence, "C", the letter "E" denotes a section of the RNA molecule having approximately 10 to 3,000 nucleotides which have affinity to second consensus sequence of said RNA-binding protein and which are capable of binding to said protein component, and the letter "F" denotes a section of the RNA molecule having 10 to 100,000 nucleotides which section is capable of being received by an RNA replicase and with another sequence, "A", being replicated; said the first and the second RNA molecules are capable of forming a third RNA molecule having the following formula:

5'-A-B-C-D-E-F-3';

said third RNA molecule formed by ligating the C and D sections, as the E and the B sections are bound to said two consensus sequences of the same RNA-binding protein, said third RNA capable of being received by an RNA replicase and being replicated by such enzyme.

2. The RNA molecules of claim 1 wherein said sequences represented by the letters "A" and "F" are selected from the group of sequences consisting of Q-beta RNA templates, MDV-I RNA, Q-beta microvariant RNA, nanovariant RNA, and midivariant RNA, and modifications of such sequences which maintain the ability of the sequences to be replicated by Q-beta replicase.

3. The RNA molecules of claim 1 wherein the sections B and E bind to RNA-binding protein through non-nucleic acid pairing interactions.

4. The RNA molecules of claim 1 wherein said RNA-binding protein is derived from a living organism.

5. The RNA molecules of claim 1 wherein the B and E sections have at least one sequence of a naturally occurring RNA component.

6. The RNA molecules of claim 1 wherein the sections C and D together define a site for ligation.

7. A method of determining the presence or absence of an RNA-binding protein having a protein component and a RNA component, said method comprising the following steps:

a) providing a first RNA molecule and a second RNA molecule, said first RNA molecule capable of binding to one consensus sequence of said protein component said RNA-binding protein and having the following formula:

5'-A-B-C-3';

wherein A is a section of the RNA molecule having 10–100,000 nucleotides which section is capable of being received by an RNA replicase and with another RNA sequence, F, being replicated, the letter "B" denotes a section of the RNA molecule having approximately 10 to 3,000 nucleotides which have affinity to one consensus sequence of said RNA-binding protein and which are capable of binding to said protein component, and the letter "C" denotes a section of the RNA molecule having approximately 1 to 20 nucleotides which section is capable of being ligated to another RNA sequence, "D" of the second RNA and said second RNA molecule is capable of binding to another consensus sequence of said protein component of said RNA-binding protein and having the following formula:

5'-D-E-F-3';

wherein D is a section of the RNA molecule having approximately 1 to 2O nucleotides which section is capable being ligated with another RNA sequence, "C", the letter "E" denotes a section of the RNA molecule having approximately 10 to 3,000 nucleotides which have affinity to second consensus sequence of said RNA-binding protein and which are capable of binding to said protein component, and the letter "F" denotes a section of the RNA molecule having 10 to 100,000 nucleotides which section is capable of being received by an RNA replicase and with another sequence, "A", being replicated; said first and the second RNA molecules are capable of forming a third RNA molecule having the following formula:

5'-A-B-C-D-E-F-3';

said third RNA molecule formed by ligating the C and D sections, as the E and the B sections are bound to two separate consensus sequence of said protein component of said RNA-binding protein, said third RNA molecule capable of being received by an RNA replicase and being replicated by such enzyme as an indication of the presence or absence of said RNA-binding protein;

b) combining a sample potentially containing said RNA-binding protein with said first and said second RNA molecules and imposing conditions which allow said first and said second RNA molecules and said RNA-binding protein to form a ternary molecule complex with first and second RNA;

c) imposing RNA ligase conditions on a said sample to form said third RNA molecule in the presence of said RNA-binding protein;

d) imposing amplification conditions on a said sample to form an amplification product in the presence of said RNA-binding protein; and e) monitoring the sample for the presence or absence of the third RNA molecule as indicative of the presence or absence of said RNA-binding protein which presence of the third RNA molecule or corresponding RNA or DNA indicates the presence of the RNA-binding protein.

8. The method of claim 7 further comprising the step of removing first and second RNA molecules which do not form a complex with RNA-binding protein.

9. The method of claim 8 wherein said first and second RNA molecules which do not form a complex are removed by filtration.

10. The method of claim 7 wherein said amplification conditions comprise combining said samples potentially containing said third RNA molecule with the enzyme Q-beta replicase.

11. The method of claim 7 wherein said sections denoted by the letters "B" and "E" have one or more sequences of the RNA component obtained from a living organism.

12. The method of claim 7 wherein the sections denoted by the letters "A" and "F" represent sequences selected from the group consisting of Q-beta RNA templates, MDV-1 RNA, Q-beta microvariant RNA, midivariant RNA, and nanovariant RNA, or modifications thereof which permit the RNA to maintain its reproducibility.

13. A kit for determining the presence or absence of a RNA-binding protein said RNA-binding protein having a protein component and a RNA component comprising a first ribonucleic acid (RNA) molecule and a second RNA molecule, ligase means and amplification means, said first RNA molecule capable of binding to RNA-binding protein and having the following formula:

5'-A-B-C-3';

wherein A is a section of the RNA molecule having 10–100,000 nucleotides which section is capable of being received by an RNA replicase and with another RNA sequence, F, being replicated, the letter "B" denotes a section of the RNA molecule having approximately 10 to 3,000 nucleotides which have affinity to one consensus sequence of said RNA-binding protein and which are capable of binding to said protein component, and the letter "C" denotes a section of the RNA molecule having approximately 1 to 20 nucleotides which section is capable of being ligated to another RNA sequence, "D" of the second RNA and said second RNA molecule is capable of binding to RNA-binding protein and has the following formula:

5'-D-E-F-3';

wherein D is a section of the RNA molecule having approximately 1 to 20 nucleotides which section is capable being ligated with another RNA sequence, "C", the letter "E" denotes a section of the RNA molecule having approximately 10 to 3,000 nucleotides which have affinity to second consensus sequence of said RNA-binding protein and which are capable of binding to said protein component, and the letter "F" denotes a section of the RNA molecule having 10 to 100,000 nucleotides which section is capable of being received by an RNA replicase and with another sequence, "A", being replicated, said first and the second RNA molecules are capable of forming a third RNA molecule having the following formula:

5'-A-B-C-D-E-F-3';

said third RNA molecule formed by ligating the C and D sections, as the E and the B sections are bound to said RNA-binding protein component, said third RNA molecule capable of being received by an RNA replicase and being replicated by such enzyme as an indication of the presence or absence of said RNA-binding protein; said ligase means capable of forming said third, hybrid RNA molecule in the presence of said complex and said amplification means capable of forming a plurality of said third RNA molecules or corresponding RNA or DNA molecule in the presence of the said third, hybrid molecule which presence of the third RNA molecule or corresponding RNA or DNA indicates the presence of the RNA-binding protein.

* * * * *

SEQUENCE LISTING

```
<160> NUMBER OF SEQ ID NOS:  25

<210> SEQ ID NO 1
<211> LENGTH: 69
<212> TYPE: RNA
<213> ORGANISM: Artificial Sequence
<220> FEATURE:
<223> OTHER INFORMATION: Description of Artificial Sequence:  ligand
      sequence

<400> SEQUENCE: 1

ggggaccccc ccggaagggg gggacgaggu gcgggcaccu cguacgggag uucgaccgug     60

acgcucuag                                                             69


<210> SEQ ID NO 2
<211> LENGTH: 166
<212> TYPE: RNA
<213> ORGANISM: Q-beta bacteriophage

<400> SEQUENCE: 2

agaucuagag cacgggcuag cgcuuucgcg cucucccagg ugacgccucg ugaagaggcg     60

cgaccuucgu gcguuucggu gacgcacgag aaccgccacg cugcuucgca gcguggcucc    120

uucgcgcagc ccgcugcgcg aggugacccc ccgaaggggg guuccc                   166


<210> SEQ ID NO 3
<211> LENGTH: 37
<212> TYPE: RNA
<213> ORGANISM: Q-beta bacteriophage

<400> SEQUENCE: 3
```

-continued

```
ggggaaaucc uguuaccagg auaacggggu uuccuca                               37


<210> SEQ ID NO 4
<211> LENGTH: 54
<212> TYPE: RNA
<213> ORGANISM: Q-beta bacteriophage

<400> SEQUENCE: 4

ccucucuacu cgaaaguuag agaggacaca cccggaucua gccgggucaa ccca            54


<210> SEQ ID NO 5
<211> LENGTH: 234
<212> TYPE: RNA
<213> ORGANISM: Q-beta bacteriophage

<400> SEQUENCE: 5

ggggaccccc ccggaagggg gggacgaggu gcgggcaccu cguacgggag uucgaccgug      60

acgcucuaga gaucuagagc acgggcuagc gcuuucgcgc ucucccaggu gacgccucgu     120

gaagaggcgc gaccuucgug cguuucggug acgcacgaga accgccacgc ugcuucgcag     180

cguggcuccu ucgcgcagcc cgcugcgcga ggugaccccc gaaggggggu uccc           234


<210> SEQ ID NO 6
<211> LENGTH: 50
<212> TYPE: DNA
<213> ORGANISM: adeno-associated virus 2

<400> SEQUENCE: 6

cgcgttcgtc ctcactctct tccgcatcgc tgtctgcgag ggccagggcc                 50


<210> SEQ ID NO 7
<211> LENGTH: 37
<212> TYPE: DNA
<213> ORGANISM: adeno-associated virus 2

<400> SEQUENCE: 7

tcgaggccct ggccctcgca gacagcgatg agctccc                               37


<210> SEQ ID NO 8
<211> LENGTH: 33
<212> TYPE: DNA
<213> ORGANISM: adeno-associated virus 2

<400> SEQUENCE: 8

gggagctcat cgctgtctgc gagggccagg gcc                                   33


<210> SEQ ID NO 9
<211> LENGTH: 22
<212> TYPE: DNA
<213> ORGANISM: adeno-associated virus 2

<400> SEQUENCE: 9

aagagagtga ggacgaacgc gc                                               22


<210> SEQ ID NO 10
<211> LENGTH: 26
<212> TYPE: DNA
<213> ORGANISM: adeno-associated virus 2

<400> SEQUENCE: 10

tcgagcgcgt tcgtcctcac tctctt                                           26
```

-continued

<210> SEQ ID NO 11
<211> LENGTH: 25
<212> TYPE: RNA
<213> ORGANISM: Artificial Sequence
<220> FEATURE:
<223> OTHER INFORMATION: Description of Artificial Sequence: probe sequence for adeno virus

<400> SEQUENCE: 11
gggaagagag ugaggacgaa cgcgc 25

<210> SEQ ID NO 12
<211> LENGTH: 30
<212> TYPE: RNA
<213> ORGANISM: Artificial Sequence
<220> FEATURE:
<223> OTHER INFORMATION: Description of Artificial Sequence: probe for adeno virus

<400> SEQUENCE: 12
ggcccuggcc cucgcagaca gcgaugagcu 30

<210> SEQ ID NO 13
<211> LENGTH: 50
<212> TYPE: DNA
<213> ORGANISM: adeno-associated virus 2

<400> SEQUENCE: 13
cgcgttcgtc ctcactctct tccgcatcgc tgtctgcgag ggccagggcc 50

<210> SEQ ID NO 14
<211> LENGTH: 54
<212> TYPE: RNA
<213> ORGANISM: Artificial Sequence
<220> FEATURE:
<223> OTHER INFORMATION: Description of Artificial Sequence: ligated probes

<400> SEQUENCE: 14
ggcccuggcc cucgcagaca gcgaugagcu gggaagagag ugaggacgaa cgcg 54

<210> SEQ ID NO 15
<211> LENGTH: 66
<212> TYPE: DNA
<213> ORGANISM: Homo sapiens

<400> SEQUENCE: 15
tcgaggggtt gcggagggtg ggcctgggag gggtggtggc cattttttgt ctaaccctac 60
tgagaa 66

<210> SEQ ID NO 16
<211> LENGTH: 62
<212> TYPE: DNA
<213> ORGANISM: Homo sapiens

<400> SEQUENCE: 16
ttctcagtag ggttagacaa aaaatggcca ccacccctcc caggcccacc ctccgcaacc 60
cc 62

<210> SEQ ID NO 17
<211> LENGTH: 93
<212> TYPE: DNA
<213> ORGANISM: Homo sapiens

<400> SEQUENCE: 17

-continued aagaagggcg taggcgccgt gcttttgctc cccgcgcgct gtttttctcg ctgactttca 60
gcgggcggaa aagcctcggc ctgccgcctt cgt 93

<210> SEQ ID NO 18
<211> LENGTH: 97
<212> TYPE: DNA
<213> ORGANISM: Homo sapiens

<400> SEQUENCE: 18
tcgaacgaag gcggcaggcc gaggcttttc cgcccgctga aagtcagcga gaaaaacagc 60
gcgcggggag caaaagcacg gcgcctacgc ccttctt 97

<210> SEQ ID NO 19
<211> LENGTH: 112
<212> TYPE: DNA
<213> ORGANISM: Artificial Sequence
<220> FEATURE:
<223> OTHER INFORMATION: Description of Artificial Sequence: ligand for
Y-1 domain with MDV-1 sequences

<400> SEQUENCE: 19
attatgctga gtgatatccc ctttaggaca atggtcctat tgccccaaag gagacccaac 60
gcctcccacc cggaccctcc ccaccaccgg taaaaaacag attgggatga ct 112

<210> SEQ ID NO 20
<211> LENGTH: 169
<212> TYPE: DNA
<213> ORGANISM: Artificial Sequence
<220> FEATURE:
<223> OTHER INFORMATION: Description of Artificial Sequence: ligand for
Y-2 domain with MDV-1 sequences

<400> SEQUENCE: 20
attatgctga gtgatatccc ttcccgcatc cgcggcacga aaacgagggg cgcgcgacaa 60
aaagagcgac tgaaagtcgc ccgccttttc ggagccggcg ccttttcgga gccggccaga 120
gatgacgttt caatctctcc tgtgtgggcc tagatcggcc cagttgggt 169

<210> SEQ ID NO 21
<211> LENGTH: 9
<212> TYPE: RNA
<213> ORGANISM: Artificial Sequence
<220> FEATURE:
<223> OTHER INFORMATION: Description of Artificial Sequence: ligand
sequences

<400> SEQUENCE: 21 ugggcgcag 9

<210> SEQ ID NO 22
<211> LENGTH: 11
<212> TYPE: RNA
<213> ORGANISM: Artificial Sequence
<220> FEATURE:
<223> OTHER INFORMATION: Description of Artificial Sequence: ligand
sequence

<400> SEQUENCE: 22
cugacgguac a 11

<210> SEQ ID NO 23
<211> LENGTH: 33
<212> TYPE: RNA

-continued

```
<213> ORGANISM: Artificial Sequence
<220> FEATURE:
<223> OTHER INFORMATION: Description of Artificial Sequence:  ligand
      sequence
<221> NAME/KEY: misc_difference
<222> LOCATION: (1)..(33)
<223> OTHER INFORMATION: Different nucleotides may be used where N is
      indicated.

<400> SEQUENCE: 23

nugggcgcag nagcugggaa ncugacggua can                              33


<210> SEQ ID NO 24
<211> LENGTH: 9
<212> TYPE: RNA
<213> ORGANISM: Artificial Sequence
<220> FEATURE:
<223> OTHER INFORMATION: Description of Artificial Sequence:ligand
      sequence

<400> SEQUENCE: 24

ugggcgcag                                                          9


<210> SEQ ID NO 25
<211> LENGTH: 11
<212> TYPE: RNA
<213> ORGANISM: Artificial Sequence
<220> FEATURE:
<223> OTHER INFORMATION: Description of Artificial Sequence:  ligand
      sequence

<400> SEQUENCE: 25

cugacgguac a                                                      11
```